(12) United States Patent
Cheung et al.

(10) Patent No.: US 8,613,776 B2
(45) Date of Patent: Dec. 24, 2013

(54) SYSTEMS AND METHODS FOR FORMING PATTERNED EXTRACELLULAR MATRIX MATERIALS

(75) Inventors: Yuk Kee Cheung, New York, NY (US); Samuel K. Sia, New York, NY (US); Curtis D. Chin, New York, NY (US); Brian Michael Gillette, Bronx, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 292 days.

(21) Appl. No.: 12/810,468

(22) PCT Filed: Dec. 29, 2008

(86) PCT No.: PCT/US2008/088486
§ 371 (c)(1),
(2), (4) Date: Sep. 9, 2010

(87) PCT Pub. No.: WO2009/086535
PCT Pub. Date: Jul. 9, 2009

(65) Prior Publication Data
US 2011/0015739 A1    Jan. 20, 2011

Related U.S. Application Data

(60) Provisional application No. 61/109,819, filed on Oct. 30, 2008, provisional application No. 61/017,070, filed on Dec. 27, 2007.

(51) Int. Cl.
*A61F 2/02* (2006.01)
(52) U.S. Cl.
USPC ...................................................... 623/23.72

(58) Field of Classification Search
USPC ...................................................... 623/23.72
See application file for complete search history.

(56) References Cited

U.S. PATENT DOCUMENTS 4,060,081 A * 11/1977 Yannas et al. .............. 623/15.12
4,970,298 A * 11/1990 Silver et al. ................... 530/356

(Continued)

FOREIGN PATENT DOCUMENTS

WO    WO 2006003442 A2 *  1/2006

OTHER PUBLICATIONS

Albrecht et al., "Multiphase electropatterning of cells and biomaterials," Lab on a Chip, 2007, 7: 702-709.

(Continued)

*Primary Examiner* — David Isabella
*Assistant Examiner* — Jacqueline Woznicki
(74) *Attorney, Agent, or Firm* — Miles & Stockbridge, P.C.; Mark A. Catan

(57) ABSTRACT

An extracellular matrix (ECM)-based scaffold suitable for artificial skin as well as other structures can be formed using a bioreactor fabricated with a pattern that introduces desired structural features, on the microscale and/or nanoscale, to ECM-precursors gelled in the bioreactor. The bioreactor can produce a finely patterned scaffold—over clinically relevant size scales—sufficiently robust for routine handling. Preformed ECM-based scaffolds can also have microscale and/or nano-scale structural features introduced into a surface thereof. ECM-based scaffolds may be formed with well-defined structural features via microetching and/or remodeling via 'contact degradation.' A surface-activated pattern can be used to degrade the ECM-based scaffold at contact regions between the pattern and the ECM. The produced ECM-based scaffolds can have structures of dimensions conducive to host tissue ingrowth while preserving the fibrous structure and ligand density of natural ECMs.

22 Claims, 13 Drawing Sheets

(56) References Cited

U.S. PATENT DOCUMENTS

| | | | |
|---|---|---|---|
| 5,830,507 | A | 11/1998 | Armstrong |
| 6,083,523 | A | 7/2000 | Dionne et al. |
| 6,156,572 | A | 12/2000 | Bellamkonda et al. |
| 6,686,184 | B1 | 2/2004 | Anderson et al. |
| 6,916,640 | B2 | 7/2005 | Yu et al. |
| 6,949,252 | B2 | 9/2005 | Mizuno et al. |
| 7,029,689 | B2 | 4/2006 | Berglund et al. |
| 2002/0082698 | A1 | 6/2002 | Parenteau et al. |
| 2002/0172705 | A1 | 11/2002 | Murphy et al. |
| 2003/0105525 | A1* | 6/2003 | Vyakarnam et al. ....... 623/15.12 |
| 2006/0141012 | A1 | 6/2006 | Gingras |
| 2006/0270032 | A1 | 11/2006 | Bhatia et al. |
| 2008/0145357 | A1 | 6/2008 | Story et al. |
| 2010/0278798 | A1 | 11/2010 | Sia et al. |

OTHER PUBLICATIONS

Albrecht et al., "Probing the role of multicellular organization in three-dimensional microenvironments," Nature Methods, Apr. 2006, 3(5): 369-375.

Balasubramani et al., "Skin substitutes: a review," Journal of the International Society for Burn Injuries, Aug. 2001, 27(5): 534-544.

Baskaran et al., "Dynamics of Tissue Neutrophil Sequestration after Cutaneous Burns in Rats," Journal of Surgical Research, Sep. 2000, 93(1): 88-96.

Bell et al., "Living tissue formed in vitro and accepted as skin-equivalent tissue of full thickness," Science, Mar. 1981, 211: 1052-1054.

Bell et al., "Production of a tissue-like structure by contraction of collagen lattices by human fibroblasts of different proliferative potential in vitro," Proceedings of the National Academy of Sciences of the United States of America, Mar. 1979, 76(3): 1274-1278.

Boontheekul et al., "Controlling alginate gel degradation utilizing partial oxidation and bimodal molecular weight distribution," Biomaterials, 2005, 26(15): 2455-2465.

Boyce et al., "Principles and practices for treatment of cutaneous wounds with cultured skin substitutes," The American Journal of Surgery, Apr. 2002, 183(4): 445-456.

Brightman et al., "Time-lapse confocal reflection microscopy of collagen fibrillogenesis and extracellular matrix assembly in vitro," Biopolymers, Sep. 2000, 54(3): 222-234.

Burke et al., "Successful Use of a Physiologically Acceptable Artificial Skin in the Treatment of Extensive Burn Injury," Annals of Surgery, Oct. 1981, 194(4): 413-428.

Cabodi et al., "A Microfluidic Biomaterial," Journal of the American Chemical Society, 2005, 127(40): 13788-13789.

Campbell et al., "A multi-station culture force monitor system to study cellular contractility," Journal of Biomechanics, 2003, 36(1):137-140.

Cha et al., "Stem cells in cutaneous wound healing," Clinics in Dermatology, Jan.-Feb. 2007, 25(1): 73-78.

Cheung et al., "Direct patterning of composite biocompatible microstructures using microfluidics," Lab on a Chip, 2007, 7: 574-579.

Choi et al., "Microfluidic scaffolds for tissue engineering," Nature Materials, Sep. 2007, 6: 908-915.

Chrobak et al., "Formation of perfused, functional microvascular tubes in vitro," Microvascular Research, May 2006, 71(3): 185-196.

Dagalakis et al., "Design of an artificial skin. Part III. Control of pore structure," Journal of Biomedical Materials Research, Jul. 1980, 14(4): 511-528.

Davis et al., "Molecular basis of endothelial cell morphogenesis in three-dimensional extracellular matrices," The Anatomical Record Part A: Discoveries in Molecular, Cellular, and Evolutionary Biology, 2002, 268(3): 252-275.

Downing et al., "The influence of microtextured basal lamina analog topography on keratinocyte function and epidermal organization," Journal of Biomedical Materials Research, Jan. 2005, 72A(1): 47-56.

Drury et al., "Hydrogels for tissue engineering: scaffold design variables and applications," Biomaterials, Nov. 2003, 24(24): 4337-4351.

Engler et al., "Matrix Elasticity Directs Stem Cell Lineage Specification," Cell, 2006, 126(4):pp. 677-689.

Fibracol Plus Collagen Wound Dressing with Alginate Product Information [online]. Johnson & Johnson, 2008 [retrieved on Oct. 8, 2008]. Retrieved from the Internet: URL: http://www.jnjgateway.com/home.jhtml?page=viewContent&contentId=09008b9880ec93fd&loc=USENG.

Franzesi et al., "A Controlled-Release Strategy for the Generation of Cross-Linked Hydrogel Microstructures," Journal of the American Chemical Society, 2006, 128(47): 15064-15065.

Freyman et al., "Fibroblast contraction of a collagen-GAG matrix," Biomaterials, 2001, 22(21): 2883-2891.

Golden et al., "Fabrication of microfluidic hydrogels using molded gelatin as a sacrificial element," Lab on a Chip, 2007, 7(6): 720-725.

Gray et al., "Retention of insulin in alginate gel beads," Biotechnology and Bioengineering, Apr. 1988, 31(6): 607-612.

Griffith et al., "Capturing complex 3D tissue physiology in vitro," Nature Review: Molecular Cell Biology, Mar. 2006, 7(3): 211-224.

Haines et al., "Light-Activated Hydrogel Formation via the Triggered Folding and Self-Assembly of a Designed Peptide," Journal of the American Chemical Society, 2005, 127(48): 17025-17029.

Hanthamrongwit et al., "Chondroitin-6-sulphate incorporated into collagen gels for the growth of human keratinocytes: the effect of cross-linking agents and diamines," Biomaterials, 1996, 17(8): 775-780.

Harada et al., "A simple combined floating and anchored collagen gel for enhancing mechanical strength of culture system," Journal of Biomedical Materials Research, Jan. 2007, 80A(1):123-130.

Helm et al., "Engineered blood and lymphatic capillaries in 3-D VEGF-fibrin-collagen matrices with interstitial flow," Biotechnology and Bioengineering, 2007, 96(1): 167-176.

Hollister, S. J., "Porous scaffold design for tissue engineering," Nature Materials, Jul. 2005, 4(7): 518-524.

Isenberg et al., "Endothelialization and flow conditioning of fibrin-based media-equivalents," Annals of Biomedical Engineering, Jun. 2006, 34(6): 971-985.

Jaksic et al., "The Use of 'Artificial Skin' for Burns," Annual Review of Medicine, Feb. 1987, 38:107-117.

Jeong et al., "Biologically Inspired Artificial Compound Eyes," Science, Apr. 2006, 312: 557-561.

Ji et al., "Generation and Differentiation of Human Embryonic Stem Cell-Derived Keratinocyte Precursors," Tissue Engineering, Apr. 2006, 12(4): 665-679.

Jones et al., "A guide to biological skin substitutes," British Journal of Plastic Surgery, Apr. 2002, 55(3): 185-193.

Kamei et al., "Endothelial tubes assemble from intracellular vacuoles in vivo," Nature, 2006, 442(7101): p. 453-456.

Khademhosseini et al., "Microscale Technologies for Tissue Engineering and Biology," Proceedings of the National Academy of Sciences of the United States of America, 2006, 103: 2480-2487.

Kopp et al., "Effect of collagen crosslinking on collagen-water interactions (a DSC investigation)," Matrix, 1989, 9(6): 443-450.

Lee et al., "Collagen mimetic peptide-conjugated photopolymerizable PEG hydrogel," Biomaterials, Oct. 2006, 27(30): 5268-5276.

Lee et al., "Integration of layered chondrocyte-seeded alginate hydrogel scaffolds," Biomaterials, 2007, 28(19): 2987-2993.

Lee et al., "Microfluidic alignment of collagen fibers for in vitro cell culture," Biomedical Microdevices, Mar. 2006, 8(1): 35-41.

Leikin et al., "Raman spectral evidence for hydration forces between collagen triple helices," Proceedings of the National Academy of Sciences of the United States of America, Oct. 1997, 94(21): 11312-11317.

Ling et al., "A cell-laden microfluidic hydrogel," Lab on a Chip, 2007, 7(6): 756-762.

MacNeil, S., "Progress and opportunities for tissue-engineered skin," Nature, Feb. 2007, 445(7130): 874-880.

Mapili et al., "Laser-layered microfabrication of spatially patterned functionalized tissue-engineering scaffolds," Journal of Biomedical Materials Research Part B: Applied Biomaterials, Nov. 2005, 75B(2): 414-424.

(56) References Cited

OTHER PUBLICATIONS

Marenzana et al., "A collagen-based interface construct for the assessment of cell-dependent mechanical integration of tissue surfaces," Cell and Tissue Research, 2007, 327(2): 293-300.
Martin, P., "Wound Healing—Aiming for Perfect Skin Regeneration," Science, Apr. 1997, 276: 75-81.
Masuda et al., "A novel two-step method for the formation of tissue-engineered cartilage by mature bovine chondrocytes: the alginate-recovered-chondrocyte (ARC) method," Journal of Orthopaedic Research, Jan. 2003, 21(1): 139-148.
Meshel et al., "Basic mechanism of three-dimensional collagen fibre transport by fibroblasts," Nature Cell Biology, 2005, 7(2): 157-164.
Mikos et al., "Engineering complex tissues," Tissue Engineering, Dec. 2006, 12(12): 3307-3339.
Miles et al., "The Role of the $\alpha 2$ Chain in the Stabilization of the Collagen Type I Heterotrimer: A Study of the Type I Homotrimer in oim Mouse Tissues," Journal of Molecular Biology, Aug. 2002, 321(5): 797-805.
Nelson et al. "Microstructured extracellular matrices in tissue engineering and development," Current Opinion in Biotechnology, Oct. 2006, 17(5): 518-523.
Nelson et al., "Tissue Geometry Determines Sites of Mammary Branching Morphogenesis in Organotypic Cultures," Science, 2006, 314: 298-300.
O'Brien et al., "Influence of freezing rate on pore structure in freeze-dried collagen-GAG scaffolds," Biomaterials, Mar. 2004, 25(6): 1077-1086.
O'Brien et al., "The effect of pore size on cell adhesion in collagen-GAG scaffolds," Biomaterials, Feb. 2005, 26(4): 433-441.
Osborne et al., "Investigation into cell growth on collagen/chondroitin-6-sulphate gels: the effect of crosslinking agents and diamines," Journal of Materials Science: Materials in Medicine, Apr. 1997, 8(4):179-184.
Osborne et al., "Investigation into the biological stability of collagen/chondroitin-6-sulphate gels and their contraction by fibroblasts and keratinocytes: the effect of crosslinking agents and diamines," Biomaterials, Feb. 1999, 20(3): 283-290.
Osborne et al., "Investigation into the tensile properties of collagen/chondroitin-6-sulphate gels: the effect of crosslinking agents and diamines," Medical and Biological Engineering and Computing, Jan. 1998, 36(1): 129-134.
Paguirigan et al., "Gelatin based microfluidic devices for cell culture," Lab on a Chip, 2006, 6(3): 407-413.
Pins et al., "Microfabrication of an analog of the basal lamina: Biocompatible membranes with complex topographies," The Journal of the Federation of American Societies for Experimental Biology, Mar. 2000, 14(3): 593-602.
Radisic et al., "Functional assembly of engineered myocardium by electrical stimulation of cardiac myocytes cultured on scaffolds," Proceedings of the National Academy of Sciences of the United States of America, Dec. 2004, 101(52): 18129-18134.
Rowe et al., "Interpenetrating collagen-fibrin composite matrices with varying protein contents and ratios," Biomacromolecules, 2006, 7(11): 2942-2948.
Rundqvist et al., "High Fidelity Functional Patterns of an Extracellular Matrix Protein by Electron Beam-Based Inactivation," Journal of the American Chemical Society, 2007, 129(1): 59-67.
Schulz et al., "Artificial Skin," Annual Review of Medicine, Feb. 2000, 51:231-244.
Sia et al., "Microfluidic devices fabricated in poly(dimethylsiloxane) for biological studies," Electrophoresis, 2003, 24(21): 3563-3576.
Sieminski et al., "The relative magnitudes of endothelial force generation and matrix stiffness modulate capillary morphogenesis in vitro," Experimental Cell Research, Jul. 2004, 297(2): 574-584.
Stenn et al., "Dispase, a Neutral Protease From *Bacillus polymyxa*, Is a Powerful Fibronectinase and Type IV Collagenase," Journal of Investigative Dermatology, Aug. 1989, 93: 287-290.
Stevens et al., "Direct patterning of mammalian cells onto porous tissue engineering substrates using agarose stamps," Biomaterials, 2005, 26(36): 7636-7641.
Supp et al. "Engineered skin substitutes: practices and potentials," Clinics in Dermatology, 2005, 23(4); 403-412.
Tan et al., "Layer-by-layer microfluidics for biomimetic three-dimensional structures," Biomaterials, Mar.-Apr. 2004, 25(7-8): 1355-1364.
Tan et al., "Microscale multilayer cocultures for biomimetic blood vessels," Journal of Biomedical Materials Research, 2005, 72A(2): 146-160.
Tang et al., "Fabrication of Collagen Gels That Contain Patterned, Micrometer-Scale Cavities," Advanced Materials, Aug. 2004, 16(15): 1345-1348.
Tang et al., "Molding of Three-Dimensional Microstructures of Gels," Journal of the American Chemical Society, 2003, 125(43): 12988-12989.
Vaikunth et al., "Endothelial progenitor cells participate in neovascularization and engraftment of cultured skin substitutes," Journal of the American College of Surgeons, Sep. 2006, 203(3): S61.
Waymack et al., "The effect of a tissue engineered bilayered living skin analog, over meshed split-thickness autografts on the healing of excised burn wounds," Journal of the International Society for Burn Injuries, Nov. 2000, 26(7): 609-619.
Weinand et al., "Comparison of hydrogels in the in vivo formation of tissue-engineered bone using mesenchymal stem cells and beta-tricalcium phosphate," Tissue Engineering, Apr. 2007, 13(4): 757-765.
Whitesides et al., "Soft lithography in biology and biochemistry," Annual review of biomedical engineering, Aug. 2001, 3: 335-373.
Wilkins et al., "Development of a bilayered living skin construct for clinical applications," Biotechnology and Bioengineering, Apr. 1994, 43(8): 747-756.
Xu et al., "Electrospun Nanofiber Fabrication as Synthetic Extracellular Matrix and Its Potential for Vascular Tissue Engineering," Tissue Engineering, Jul. 2004, 10(7-8): 1160-1168.
Yannas et al., "Design of an artificial skin. I. Basic design principles," Journal of Biomedical Materials Research, Jan. 1980, 14(1): 65-81.
Yannas et al., "Design of an artificial skin. II. Control of chemical composition," Journal of Biomedical Materials Research, Mar. 1980, 14(2): 107.
Yannas et al., "Synthesis and characterization of a model extracellular matrix that induces partial regeneration of adult mammalian skin," Proceedings of the National Academy of Sciences of the United States of America, Feb. 1989, 86:933-937.
Yannas et al., "Wound tissue can utilize a polymeric template to synthesize a functional extension of skin," Science, Jan. 1982, 215: 174-176.
Yannas, I.,V., "Collagen and Gelatin in the Solid State," Journal of Macromolecular Science: Reviews in Macromolecular Chemistry and Physics C, 1972, 7(1): 49-106.

\* cited by examiner

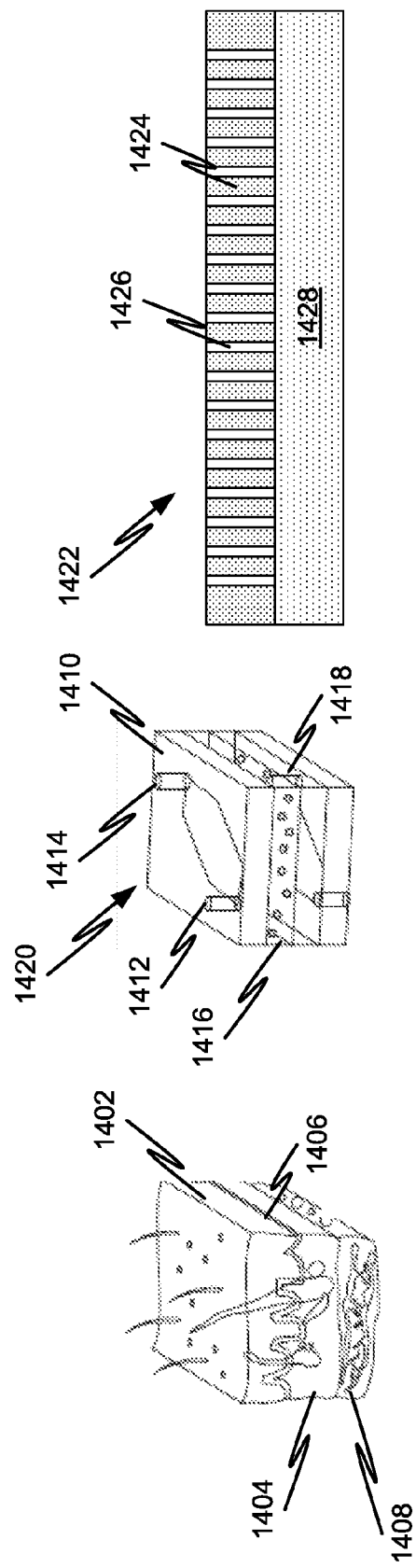

SYSTEMS AND METHODS FOR FORMING PATTERNED EXTRACELLULAR MATRIX MATERIALS

CROSS-REFERENCE TO RELATED APPLICATIONS

This application is a national stage application of International Application No. PCT/US08/88486, filed Dec. 29, 2008, which claims the benefit of U.S. Provisional Application No. 61/017,070, filed Dec. 27, 2007, and U.S. Provisional Application No. 61/109,819, filed Oct. 30, 2008, all of which are hereby incorporated by reference herein in their entireties.

BACKGROUND

Stem cells can divide to form new stem cells and to differentiate into specific cells, for example, tissue-specific cells. This makes them valuable for the repair or replacement of damaged tissues and structures which have been widely discussed. But growth of most eukaryotic animal cells, such as human cells, requires environments including surfaces to permit them to grow. A challenge in engineering tissues is mimicking the three-dimensional organization and function of living animal tissues such as the human body.

Three-dimensional extracellular matrices have been constructed in laboratories to provide an artificial environment for cells that better mimic the physical arrangement, cellular organization, and gene expression of living tissues than two dimensional cultures such as Petri dishes. Cells in collagen gels have demonstrated that cells can express natural organization and differentiation, cell-cell interactions, gene expression, and aspects of natural histology.

The manufacture of complex tissue scaffolds presents challenges. Typically, bulk properties of a matrix are adjusted so that the entire cell population can be modulated. However, such bulk changes may not be appropriate when trying to recreate the complex three-dimensional (3D) patterning, organization and regional architecture of one or more cell types in an engineered tissue construct. In such cases, techniques for controlling the local microenvironment presented to specific cell populations within a 3D construct may be desired. Even relatively simpler tissue scaffolds, such as for artificial skin applications present difficult challenges in terms of providing mechanical support, sufficient integrity to allow manipulation, while permitting host cell ingrowth.

Naturally-derived extracellular matrices (ECMs) can be used in tissue engineering, drug delivery applications and basic biological studies, due to their close resemblance (in structure and composition) to in vivo ECM. In particular, constructs can be formed into three-dimensional (3D) ECMs so as to mimic the often inhomogeneous and anisotropic properties of native tissues and to construct in vitro cellular environments. Since these 3D ECMs provide physiologically relevant cellular environments, they can be used to study tissue morphogenesis and to engineer tissue.

SUMMARY

The present disclosure is directed to systems, methods, and devices for forming extracellular matrix materials with certain defined structural features.

An ECM-based scaffold suitable for artificial skin as well as other structures can be formed using a bioreactor fabricated with a pattern that introduces desired structural features, on the microscale and/or nanoscale, to ECM-precursors gelled in the bioreactor. The bioreactor can produce a finely patterned scaffold—over clinically relevant size scales—sufficiently robust for routine handling.

Preformed ECM-based scaffolds can also have microscale and/or nano-scale structural features introduced into a surface thereof. ECM-based scaffolds may be formed with well-defined structural features via microetching and/or remodeling via "contact degradation." A surface-activated pattern can be used to degrade the ECM-based scaffold at contact regions between the pattern and the ECM. Multiple patterns can be introduced onto one or multiple surfaces of the same ECM-based scaffold so as to introduce desired structural features. The produced ECM-based scaffolds can have structures of dimensions conducive to host tissue ingrowth while preserving the fibrous structure and ligand density of natural ECMs.

BRIEF DESCRIPTION OF THE DRAWINGS

FIG. 4A is a schematic diagram of the layers of natural skin.

FIG. 4B is a schematic diagram of the layers of a porous ECM-based scaffold analog of skin.

FIG. 4C is a schematic cross-section of layers of a porous ECM-based construct.

DETAILED DESCRIPTION

Microfabrication can be used to create high-precision scaffolds and can produce multi-component structures containing extracellular matrices (ECMs), for example, collagen and basal lamina, as well as cells, such as fibroblasts, keratinocytes, melanocytes, endothelial cells, etc. Such high precision may be clinically important, especially with regard to porous features of ECM-based materials for use in tissue engineering and/or tissue substitutes. The structural aspects, such as ligand density and porosity, of an ECM-based material may directly affect cell migration and host cell ingrowth speed. Both scaffold porosity and composition affect ligand density by defining, respectively, the total surface of the structure exposed to cells and the surface density of ligands. For example, to achieve minimal scarring in patients upon wound closure, the porous features of an acellular ECM-based material containing cross-linked collagen and chondroitin-6-sulfate should be tuned to an average diameter of 20-μm to 125-μm to have sufficient ligand density for cell migration and at the same time be sufficiently porous for rapid ingrowth of host fibroblasts and endothelial cells. Cell attachment and viability are primarily influenced by scaffold specific area in collagen-glycosaminoglycan (collagen-GAG) materials.

Accordingly, the present disclosure is directed to systems, methods, and devices for forming ECM-based materials with well-defined structural features, and, in particular, for forming ECM-based scaffolds with structural features for influencing cell behavior. The resulting ECM-based scaffold may be employed as a clinically relevant structure for tissue engineering, for example, as a skin substitute.

Using a microfabricated bioreactor, clinically relevant ECM-based scaffolds, for example, centimeter-scale scaffolds, can be produced with well controlled porous features, for example, in the nanometer or micrometer range. This microfabricated bioreactor method can produce a finely patterned scaffold—over clinically relevant size scales—sufficiently robust for routine handling. Further, this microfabrication approach produces pores of dimensions conducive to host tissue ingrowth while preserving the fibrous structure and ligand density of natural ECMs and gels, such as collagen. The approach also forms a basis for engineering anatomically complex tissues made of many cellular and extracellular components, such as, but not limited to, skin substitutes.

Figure 1A:
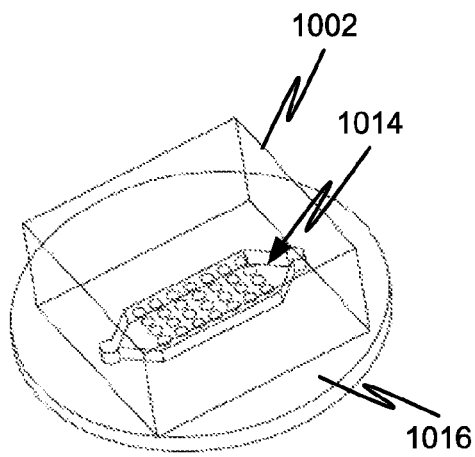
FIG. 1A is a schematic representation of a configuration for micromachining a bioreactor for a porous ECM-based scaffold.
Figure 1B:
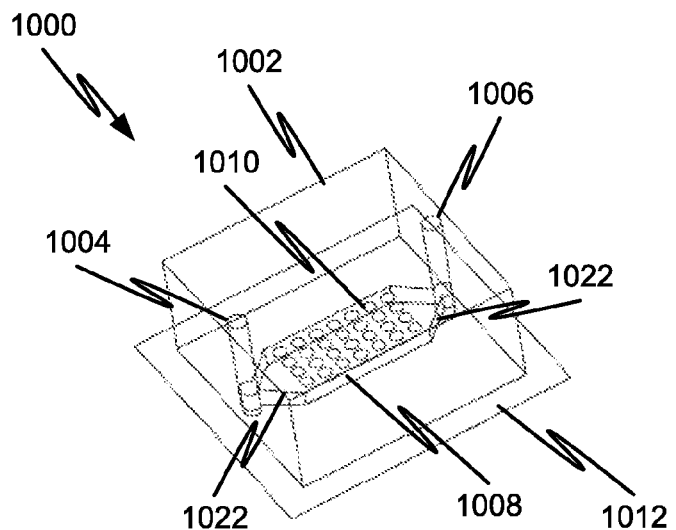
FIG. 1B is a schematic representation of a configuration for fabricating a porous ECM-based scaffold using a bioreactor.

A microfabricated bioreactor 1002 is shown in FIG. 1B. Inside the microfabricated bioreactor 1002, extracellular components and cell-encapsulated matrices are flowed between an inlet 1004 and an outlet 1006 and subsequently polymerized in situ. The chamber 1008 can contain features 1010, for example, regularly spaced cylindrical posts, which correspond to desired porous features for an ECM-based scaffold. Because of the generally planar structure of the bioreactor chamber 1008, large-sized scaffolds are able to be constructed, thereby allowing tissues of clinically relevant size scales to be formed.

Post shapes need not be circular and may include oval-shaped, polygonal-shaped, or prism-shaped posts of various types. Also, the posts need not have a uniform cross-section. From example, the posts can be tapered.

The backing 1012 of the bioreactor 1002 may be, for example, a flexible silicone elastomer layer, such as a polydimethylsiloxane (PDMS), or alternatively, a relatively rigid material, such as a glass or polymer. The bioreactor setup, as shown illustratively in FIG. 1B, allows sequential flowing and purging of different components before a polymerization step so as to facilitate the construction of spatially complex structures containing cells and extracellular matrix precursors.

A microfabricated bioreactor 1000 can be created using, for example, a soft lithographic process, such as PDMS molding on an SU-8 mold. For example, a 165-μm layer of epoxy-based photoresist SU-8 2050 may be spin-coated onto a silicon wafer 1016, exposed to 365-nm light for 100 seconds through a photomask, and developed with propylene glycol monomethyl ether acetate so as to generate a pattern 1014 of features. To construct the bioreactor 1000, PDMS 1002 can be molded onto the SU-8 master pattern to transfer the pattern 1014 of the SU-8 master to the PDMS 1002, as shown in FIG. 1A. After creating the PDMS replica mold 1002, holes can be punched through the mold to create an inlet 1004 and an outlet 1006. Alternatively, the inlet and outlet may be formed as part of the molding process. The mold may be treated with bovine serum albumin (BSA) (1% w/v in PBS) and conformally sealed to a cover 1012, such as a glass coverslip or thin PDMS membrane, as shown in FIG. 1B, to produce the microfabricated bioreactor 1000.

Additionally or alternatively, a thicker microfabricated bioreactor may be constructed by using a thicker photoresist layer for the mold. The resulting thicker microfabricated bioreactor can be used to form thicker ECM-based scaffolds. Thicker ECM-based scaffolds may in turn be used in the engineering of tissues and/or tissue substitutes, for example, a skin substitute that mimics a full-thickness dermal layer (e.g., hundreds of microns (μm)).

Microfabrication techniques other than those described herein may also be employed to create the master pattern for molding a bioreactor 1000. For example, a master may be created by semiconductor manufacturing, microelectromechanical system (MEMS) manufacturing, or polymer microfluidic manufacturing techniques, including, but not limited to, deep reactive ion etching (DRIE), reactive ion etching (RIE), focused ion beam (FIB) etching, wet etching, bulk micromachining, surface micromachining, laser micromachining, and/or X-ray lithography, electroplating, and molding (LIGA) techniques on or to a glass, semiconductor, or polymer substrate. In addition to those techniques described herein, various fabrication techniques may be employed for creating the bioreactor 1000. For example, the bioreactor may be directly created from an appropriate biocompatible polymer without a mold, such as by, but not limited to, laser micromachining, hot embossing, and/or injection molding.

A microfabricated bioreactor can be fabricated with features, for example, cylindrical posts, spanning void fractions of 20% to 60% and mean pore size of 20-μm to 125-μm, for example, 70-μm to 120 μm, although other void fractions and mean pore sizes are possible depending upon a contemplated embodiment. In general, pores with mean sizes below 20-μm may not allow for free access to fibrovascular cells while pores with mean sizes greater than 125-μm may not allow for proper cell attachment. However, optimal values for mean pore sizes may vary depending on the geometry and pattern of the pores. Further, although the pores are shown in the various figures as a regularly spaced array, irregularly spaced arrays, random distributions, and other configurations for the pores are also possible depending upon a contemplated embodiment.

A microfabricated bioreactor design can have a center channel 1008 with a grid of posts 1010 spanning, for example, about 11-mm long and 6-mm wide. These dimensions are for illustrative purposes and other sizes can be created. Accordingly, the dimensions of the center channel 1008 may be shorter or longer than these disclosed dimensions according to a particular application. The channel 1008 may have a tapered end 1022 at each side thereof. The tapered ends 1022 can minimize bubble formation in the channel 1008. The microfabricated bioreactor 1000 can be reusable, such that a single bioreactor 1000 can be used to produce a multitude of ECM-based scaffolds 1018 with corresponding pores 1020.

To construct the ECM-based scaffolds 1018, ECM precursors can be mixed and injected into the central channel 1008 of the bioreactor 1002 through inlet 1004. For example, collagen rat tail type I can be mixed with a GAG, such as chondroitin-6-sulfate ($Ch6SO_4$) from shark cartilage. This mixture can then be neutralized with sodium hydroxide (NaOH) to a pH of 7.4 to yield a final ECM concentration of 4 mg/mL collagen with 0.8 mg/mL $Ch6SO_4$.

The collagen-GAG precursors can be flowed into the microfabricated bioreactor 1000 and polymerized in situ by incubating, for example, at 37° C. for one hour. Contraction of the patterned gel may occur during gelling of the precursors in situ in the bioreactor thereby generating voids between the patterned gel and the walls of the channel of the bioreactor. To compensate for the contraction, prior to removing the patterned gel from the bioreactor, additional gel precursors, such as collagen-GAG precursors, can be reflowed into the bioreactor so as to fill the generated voids. The reflowed precursors can then be gelled in situ so as to form a part of the resulting patterned gel.

The resulting ECM-based scaffold in the bioreactor can have a first layer of gel with a plurality of substantially discontinuous zones, such as substantially non-connecting cylindrical zones, extending entirely through the thickness of the gel layer. This may be accomplished, for example, by forming the zones as through-holes or pores with uniform cross-sectional area through a depth of the gel layer.

The zones can be substantially regularly spaced. The zones can have a void fraction between 20 and 60% and a mean diameter between 20-μm and 125-μm, for example, between 70-μm and 120-μm. An average density of fibers in each zone can be lower than an average density of fibers in the gel layer between the zones. For example, the average density of fibers in each zone can be zero. Each zone can extend entirely through the thickness of the gel layer.

An average distribution of fibers in the gel layer can be uniform across the thickness of the gel first layer. The distribution of fibers can be uniform through a thickness of the gel layer, for example, at least above an areal pitch of 5-mm. The density of fibers in each zone can substantially permit migration by human epithelial dermal cells. The fibers can include a protein, such as collagen, and a glycosaminoglycan, such as chondroitin-6-sulfate. The respective densities of the fibers in the zones and between the zones can permit freer migration of host cells, for example, human epithelial dermal, into the zones than between the zones. The engineered tissue structure can also have living cells therein. A density of living cells in the zones can be greater than a density of living cells in the gel first layer between the zones.

Figure 1C:
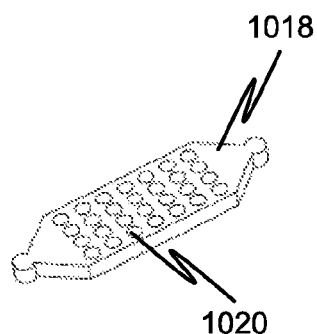
FIG. 1C is a schematic representation of a porous ECM-based scaffold.

The resulting ECM-based scaffold 1018 may be dehydrated by continued incubation, for example, at 37° C. for one day or until completely dehydrated. The dehydration of the ECM-based scaffold allows the scaffold structure to collapse, whereby the mold 1002 can be removed. The resulting ECM-based scaffold is then free of the mold 1002, as shown in FIG. 1C, and replicates therein the pattern of pores 1020 from the mold 1002.

The dehydrated scaffold can be manipulated onto a backing, such as a thin PDMS membrane, for subsequent handling. The scaffold can have a layer of ECM or gel with fibers therein. The backing can support the ECM layer thereon. The ECM layer can have a pattern extending through the thickness thereof such that a fiber density in the ECM layer is uniform through the thickness. The pattern can be pores. The ECM layer can have a mean pore size from 20-μm to 125-μm and a void fraction from 20% to 60%. The ECM can include collagen and glycosaminoglycan.

The dehydrated scaffold may be used as an engineered tissue structure, for example, as a biocompatible skin substitute. For assembly of multi-component structures and use of the ECM-based scaffolds, the dehydrated scaffold can be rehydrated by directly adding, for example, about 50 μl of 1×PBS and cell media thereto.

It is noted that using a thick-film master material, as discussed above, would evidently result in a thicker mold and thus a thicker ECM-based scaffold. The use of a thick and physically robust ECM-based scaffold may also facilitate peeling of the scaffold from the backing for use in particular applications, such as a surgical grafting or skin repair.

Lowly immunogenic, GAG serves to retard the breakdown of collagen and increase the hydration, strength and elasticity of collagen. Chondroitin-6-sulfate, a repeating disaccharide of N-acetylgalactosamine and glucuronic acid, can be selected as a suitable GAG for several reasons. Incorporation of 20% chondroitin-6-sulfate (v/v) increases collagen gel strength, with increases in Young's modulus, maximum load and stress at maximum load. Further, addition of chondroitin-6-sulfate increases the growth rate of keratinocytes seeded on collagen gels and lyophilized collagen sponges. While chondroitin-6-sulfate has been discussed above, any suitable GAG may be used in the ECM-based scaffold.

The chondroitin-6-sulfate used in the microfabricated scaffold may not be wholly covalently attached to the collagen fiber. This may preserve native extracellular matrix structure, in which collagen and GAG are not covalently cross-linked. Accordingly, this preserved structure may aid host regeneration. Also, some of the GAG may in fact be crosslinked to collagen fibers, since chondroitin-6-sulfate has previously been immobilized onto collagen fibers by condensation reactions via dehydration (between free carboxyl groups on glucuronic acid residues in the GAG chain with ϵ-amino groups of lysyl residues in collagen).

Figure 2:
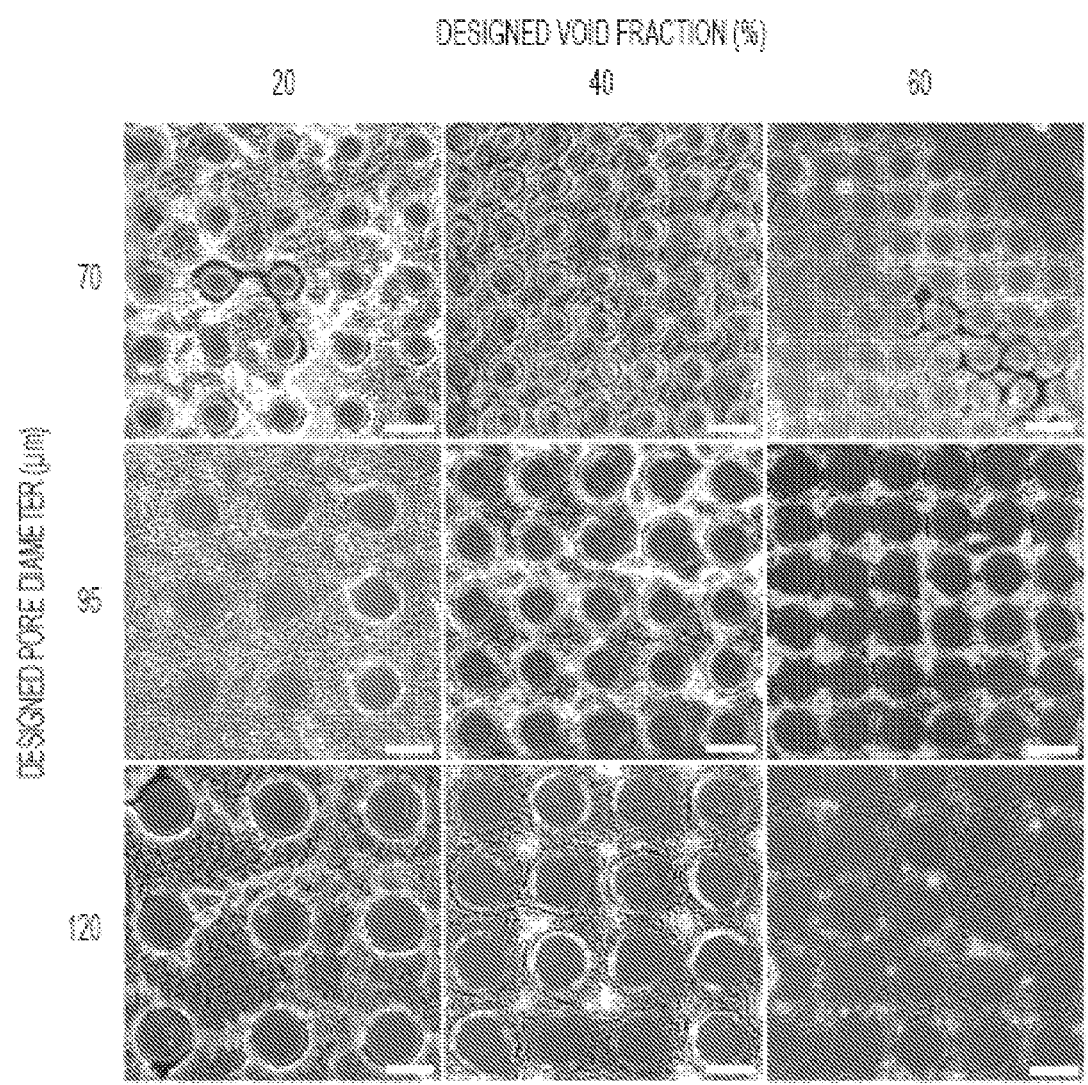
FIG. 2 shows phase-contrast images of porous ECM-based scaffolds with various pore diameters and void fractions.

Examples of the variety of pore sizes that can be obtained in a fabricated bioreactor using the technique disclosed herein are illustrated in FIG. 2. The illustrated collagen-based scaffolds have combinations of void fractions of 20%, 40%, and 60% and mean pore sizes of 70-μm, 95-μm, and 120-μm, respectively. Analysis of the images of the fabricated collagen-based scaffolds revealed that the scaffolds can be produced with well-controlled porous features, as reflected in the data of Table 1 below.

TABLE 1

Mean pore diameter (clear) and void fraction (shaded) of fabricated collagen-GAG scaffolds. Designed values are listed on the axes. Actual values with standard deviation are reported in the table.

|  |  | Designed Void Fraction (%) | | |
|---|---|---|---|---|
|  |  | 20 | 40 | 60 |
| Designed Pore Diameter (μm) | 70 | 72 ± 4 | 67 ± 3 | 69 ± 6 |
|  |  | 20 ± 1 | 35 ± 2 | 48 ± 2 |
|  | 95 | 102 ± 7 | 98 ± 4 | 93 ± 3 |
|  |  | 20 ± 2 | 40 ± 3 | 53 ± 1 |
|  | 120 | 124 ± 1 | 124 ± 4 | 121 ± 3 |
|  |  | 20 ± 0 | 40 ± 1 | 56 ± 0 |

The precise pore structure of the ECM-based scaffolding produced using the microfabricated bioreactor described can hasten cellular migration into engineered tissues, such as skin substitutes, compared to non-porous scaffolds. For example, with skin substitutes, fast cellular migration into the grafted skin substitute is important because the recruitment of mesenchymal, such as fibroblasts and endothelial cells, and epithelial cells from surrounding healthy dermal and subcutaneous tissues is necessary for tissue ingrowth as well as for drawing debrided wound margins together and establishing reepithelialization.

A cell migration assay can be performed by seeding fibroblasts onto a thin layer of Matrigel™ and placing a 40-μm thick ECM-based scaffold (either containing microfabricated pores or without pores as a control)—backed by a silicone elastomer layer—on top. Matrigel™ (BD Biosciences), which is the trade name for a gelatinous protein mixture, resembles the complex extracellular environment found in many tissues.

Figures 3A, 3B:
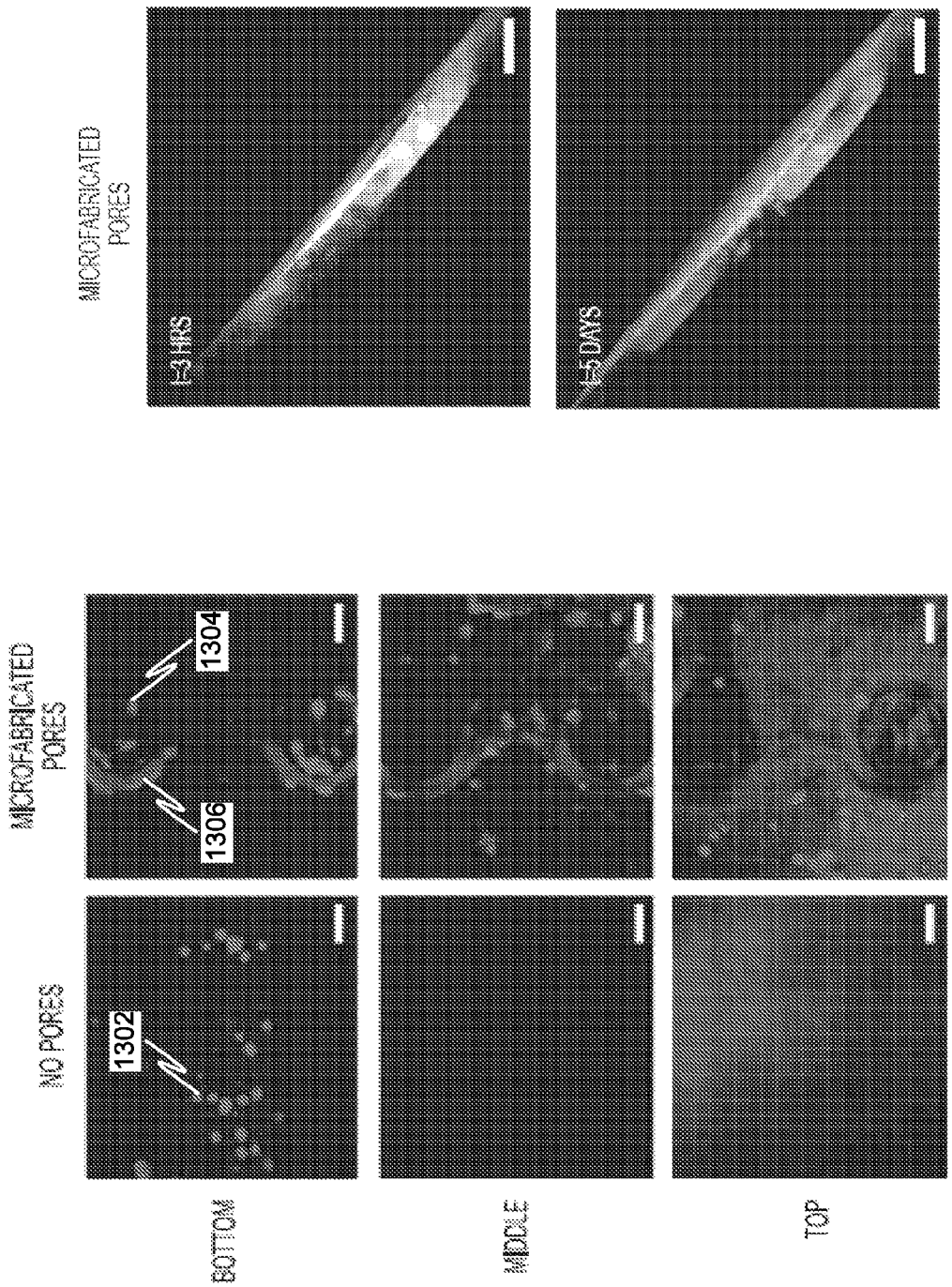
FIG. 3A illustrates cellular migration at various locations within a porous ECM-based scaffold compared to a regular non-porous ECM-based scaffold at 3 hours.
FIG. 3B illustrates cellular migration in a porous ECM-based scaffold at 3 hours after assembly and at 5 days after assembly.

FIG. 3A shows confocal fluorescence slices of bottom (interface of Matrigel™ with collagen-GAG), middle (collagen-GAG), and top (interface of collagen-GAG with PDMS) of the same composite structure. As shown in FIG. 3A, while fibroblasts 1302 in the nonporous scaffold may not migrate from the Matrigel™ at the bottom through the collagen-GAG, fibroblasts 1304 readily migrated through the microfabricated porous collagen-GAG scaffold after 3 hours. Further, fibroblasts localized near the pores 1306 at the collagen-Matrigel™ interface, but laterally dispersed as they migrated through the collagen-GAG. Thus, the fibroblasts may use the microfabricated pores 1306 as conduits for populating the collagen-GAG scaffold. As shown in the 3D reconstructed images of FIG. 3B, the fibroblasts migrate through the porous scaffold after 3 hours and further dispersed throughout the scaffold after 5 days.

The use of pores for the scaffold does not adversely the clinical use of the scaffold. Based on in vitro cellular migration studies described above, which suggest that the thru pores would likely serve as conduits for host cell repopulation (FIG. 3A-B), host remodeling should quickly fill the pores with native ECM.

The spatial fidelity of porous features in ECM-based scaffolds produced using a microfabricated bioreactor is high when compared to lyophilization, resulting in an order of magnitude improvement over lyophilized scaffolds in terms of reproducibility (measured by standard deviation) in mean pore size and void fraction. The fidelity of these porous features may be further improved by using the microfabricated bioreactor to reflow the central channel with ECM precursors even after ECM contraction or by directly patterning ECM composites in the presence of other biocompatible materials (e.g., polyethylene glycol hydrogels).

In addition to the spatial fidelity afforded by the present technique, scaffolds created using a microfabricated bioreactor can be structurally differ from scaffolds produced by lyophilization. For example, the ECM-based scaffolds made using a microfabricated bioreactor can contain two distinct regions of natural extracellular matrix and hollow pores. An advantage of this scaffold structure is that promotion of cell migration through the scaffold can be engineered independently of chemically modifying the native ECM structure. For example, a collagen region, which preserves the density of cell-attachment sites and fibrous structure of collagen fibers that affect the rate and mode of cell migration, can mimic the dermal ECM in terms of collagen concentration, composition, structure, and stiffness. This collagen region does not require chemical crosslinkers, such as glutaraldehyde, carbodiimides and diamines, or vacuum dehydration, which increases crosslink density via condensation or esterification reactions. Rather, with a natural collagen-based scaffold, the porosity of the microfabricated scaffold can be precisely fine-tuned to optimize the rate of cellular ingrowth and hence tissue regeneration in the host upon grafting.

The two distinct regions of porous ECM-based scaffolds as disclosed herein can be further characterized as a first region of well-defined pores for cell migration and a second region of natural ECM structure and density, such as a natural collagen fibrous structure with hundreds of nanometers in pore size as found in the physiological dermis. Thus, the disclosed methods can be used to produce a construct with all the components of natural tissue, which can decrease scarring in vivo and serve as realistic models for a variety of in vitro testing.

Additional tissue components can be added to the microfabricated porous ECM-based scaffold in a step-wise manner so as to produce constructs analogous to a tissue component or a biological system. As discussed above, a patterned gel layer can include a plurality of substantially discontinuous zones. A second gel layer different from a patterned gel layer can be supported on a first side of the patterned gel layer. The patterned gel layer can include collagen and the second gel layer can include a hydrogel, such as Matrigel™. Each zone in the patterned gel layer can extend entirely through the thickness of the patterned gel layer so as to connect, through each zone, the second gel layer with a second side opposite the first side of the patterned gel layer. An average density of fibers in the second gel layer can be lower than an average density of fibers in the patterned gel layer between the zones. The second gel layer can serves as a backing layer with a respective average density of fibers that is lower than the average density of fibers between the zones in the patterned gel layer.

Repairing a skin wound can include flowing gel precursors into a bioreactor. The bioreactor can have a regular pattern of cylindrical posts extending between opposite faces of the bioreactor. The cylindrical posts can have diameters between 70-μm and 120-μm. The method can also include gelling the precursors in situ to form a patterned gel. The cylindrical posts can be configured such that a pattern of pores is defined in the patterned gel. Each pore can extend entirely between opposite faces of the patterned gel. The pattern can extend across an area greater than one square centimeter. The patterned gel can include collagen and GAG. The method can also include removing the patterned gel from the bioreactor. The method can also include layering the patterned gel on a second gel. The second gel may be of the same or different type as the patterned gel or with the same or different characteristics than the patterned gel. The patterned gel can be positioned on a skin wound. Cells can be permitted to migrate into the patterned gel.

The microfabricated porous ECM-based scaffold can be incorporated with other ECM-based structures to form a skin analogue, such as the construct 1420 shown in FIG. 4B. For illustration, spatially distinct layers of natural skin (e.g., epidermis 1402, basal lamina 1404, dermis 1406, subcutaneous tissue 1408) are shown in FIG. 4A. An ECM-based construct 1420 can be assembled to mimic this layer arrangement to provide a more natural environment for the migration and growth of cells. A layer of Matrigel™ 1416, which may contain components from basal lamina, can be provided on a microfabricated porous collagen-based scaffold 1418. Also, inlet 1412 and outlet 1414 holes can be provided in a thin elastomer layer 1410, such as PDMS, that can serve as a temporary epidermal analog for possible controlled delivery of additional reagents.

FIG. 4C shows an example of an engineered tissue construct 1422. A first layer 1424 of ECM can be formed, for example, from collagen-GAG. The first layer 1424 of ECM can have a uniform distribution of fibers through a thickness of the first layer. The first layer 1424 can include a plurality of spaced non-connecting zones 1426. The average density of fibers in each zone 1426 can be less than the average density of fibers in the bulk first layer 1424, i.e., between the zones 1426.

For example, the zones can include pores or passages that extend through the thickness of the first layer 1424 of ECM. The zones can be regularly or irregularly spaced. The density of fibers within the zones can allow the migration of living cells, such as human epithelial dermal cells, into the construct 1422. The density of cells can be greater in the zones 1426 than in the bulk ECM 1424.

The construct 1422 can also include a second layer 1428 of ECM adjacent to a first side of the first layer 1424 of ECM. An average density of fibers in the second layer 1428 can be lower than an average density of fibers in the bulk ECM 1424, between zones 1426. The zones 1426 can connect the second layer 1428 with a second side of the first layer 1424 opposite to the first side.

Figure 5A:
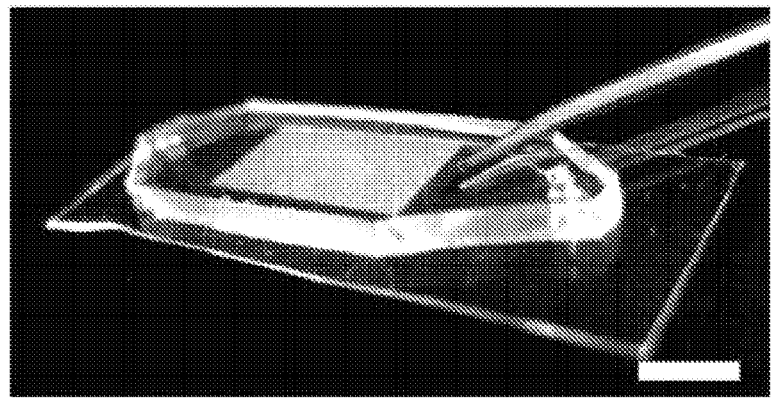
FIG. 5A is a photograph of an overall multilayer structure for fabricating a porous ECM-based scaffold analog of skin.
Figure 5B:
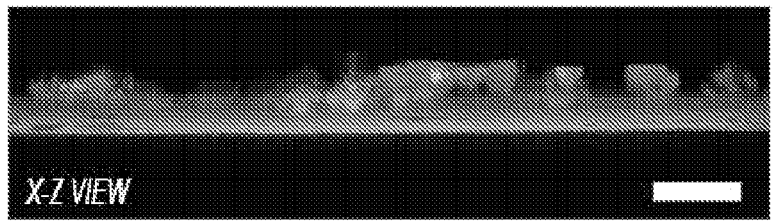
FIG. 5B is a confocal fluorescence image (x-z view) of a porous ECM-based scaffold analog of skin.
Figure 5C:
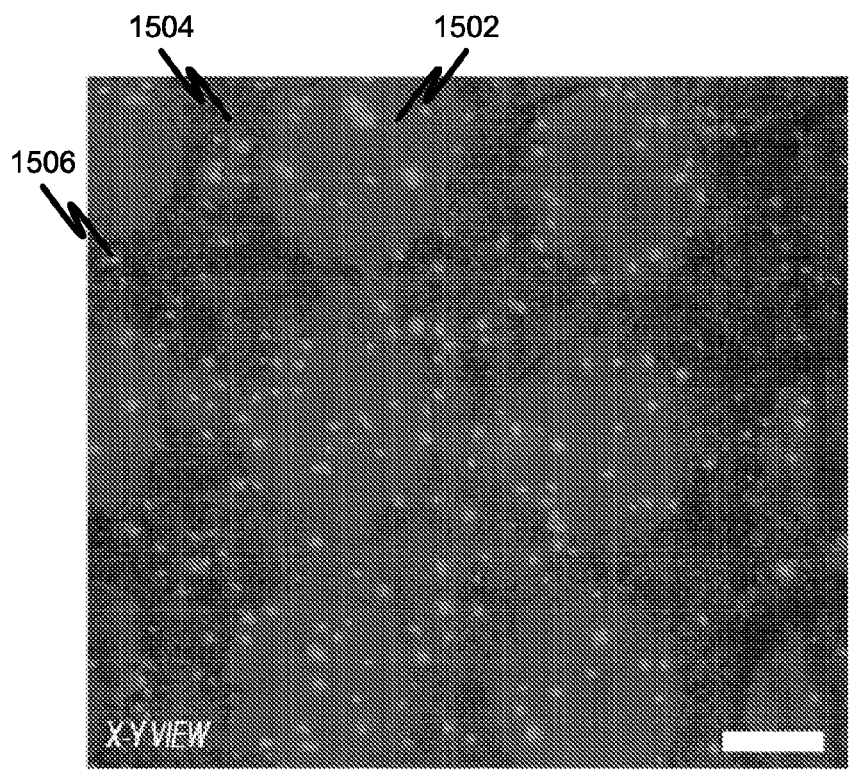
FIG. 5C is a confocal fluorescence image (x-y view) of a porous ECM-based scaffold analog of skin.

FIG. 5A shows an example of a fabricated construct similar to the construct of FIG. 4B. FIG. 5B shows a confocal image in the x-z plane of the fabricated construct of FIG. 5A. The intended spatial layering of collagen (which autofluoresces under confocal reflectance) and Matrigel™ with fluorescent cells encapsulated is apparent in FIG. 5B. FIG. 5C provides an additional top-down fluorescence image in the x-y plane of the fabricated construct. Three distinct regions are evident: a region 1502 of pores, a region 1504 of collagen fibers, and fluorescent beads 1506 in the underlying Matrigel™ layer.

A microfabricated bioreactor can be integrated with other high-throughput techniques developed for building composite structures. Further, the microfabricated bioreactor can be used in the construction of anatomically complex, biologically inspired scaffolds, such as, but not limited to, incorporation of growth factors, endothelial cells, or genetically-modified cells to produce antibacterial protein.

Figure 6A:
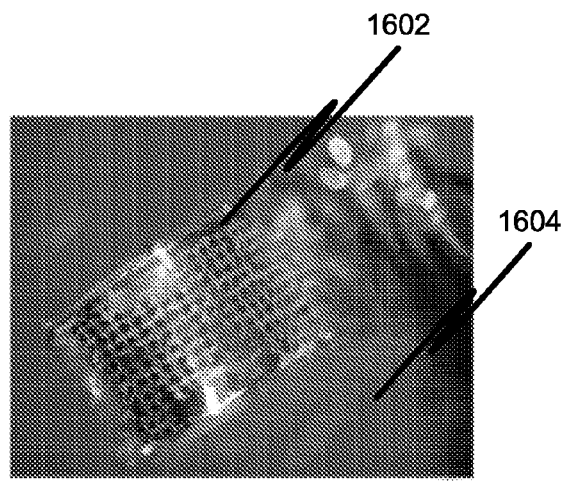
FIG. 6A shows a porous ECM-based scaffold on an elastomer backing.
Figure 6B:
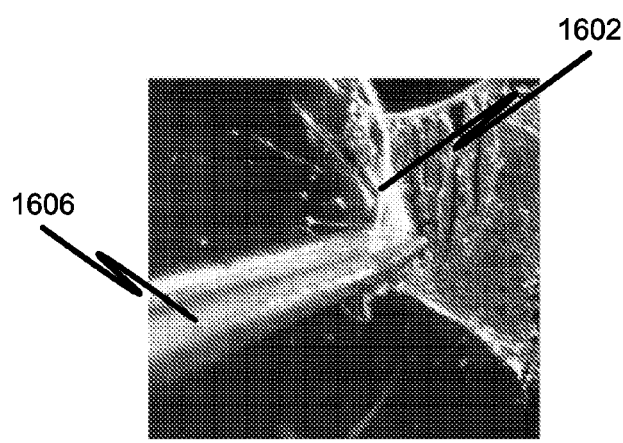
FIG. 6B shows a porous ECM-based scaffold being released from an elastomer backing.
Figure 6C:
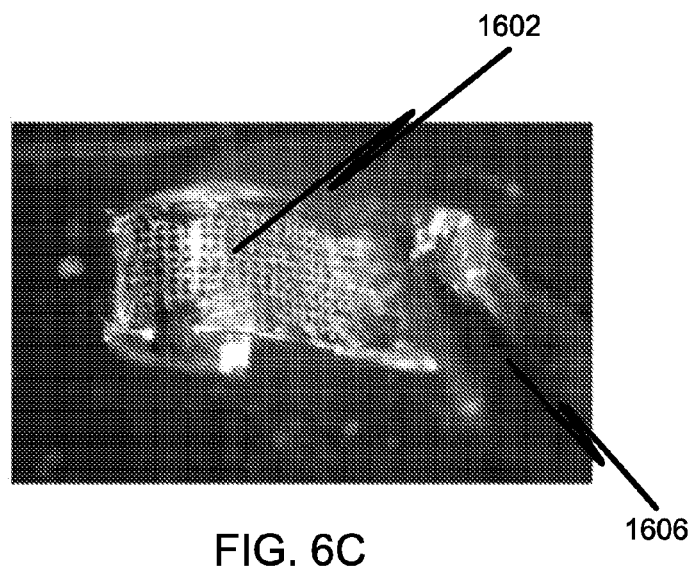
FIG. 6C shows a porous ECM-based scaffold being manipulated using forceps.

A microfabricated ECM-based scaffold can be used with a flexible silicone elastomer layer as a backing for routine handling. As shown in FIG. 6A, an ECM-based scaffold 1602 can be fabricated on top of a thin flexible elastomer member 1604. For example, the scaffold may be a collagen-GAG structure, 30-μm in thickness and 1-cm long, and with designed pore diameter of 95 μm and void fraction of 40%. The ECM-based scaffold 1602 may be carefully peeled off from the elastomer backing 1604, as shown in FIG. 6B, and handled using forceps 1606 (FIG. 6C) or other appropriate manipulators.

As the disclosed method for producing ECM-based scaffolds allows for refilling of a microfabricated bioreactor volume, spatial fidelity of scaffold features can be improved by pre-contracting the initially gelled collagen, and re-filling and re-gelling the void volume in the bioreactor. Additionally, the disclosed method is versatile for manufacturing multi-component systems since cells and extracellular components can be readily added to the scaffold. Further, the microfabricated bioreactor method can be used to fabricate centimeter-scale planar porous scaffolds, which can be a size scale relevant for tissue engineering and/or tissue replacements (e.g., skin replacement). Furthermore, the microfabricated bioreactor can be used for a diverse set of ECMs, including those matrices, such as alginate, that cross-link chemically rather than by temperature.

The present disclosure is also directed to systems, methods, and devices for microetching and/or remodeling of pre-formed ECM material, and, in particular, microetching and/or remodeling of 3D ECM materials via "contact degradation." A surface-activated pattern can be used to degrade a 3D ECM material at contact regions between the pattern and the ECM material. Since this patterning technique is subtractive rather than additive, it offers new capabilities for fabricating 3D ECM materials with microscale or smaller feature sizes. Such capabilities include, but are not limited to, real-time control of feature heights and structural remodeling of pre-existing cell-laden ECM materials. Compared to conventional etching techniques, such as surface micromachining, contact degradation differs in principle in that the pattern can be defined (and etching can be activated) by contact with a functionalized solid surface, and in that the mechanism of degradation is enzymatically mediated and hence analogous to cellular digestion of ECM materials with matrix metalloproteases.

Forming a 3D ECM construct that can be used, for example, as a biocompatible construct, can include coating at least a portion of a pattern transfer surface with a degradation agent. The pattern transfer surface can have feature sizes less than 15-μm and at least one etch stop region coated with an adhesion inhibiting agent. The pattern transfer surface having the degradation agent can be contacted with a first surface of a gel for a first predetermined period of time so as to form a pattern in the first surface. The pattern transfer surface having the degradation agent can also be contacted with a second surface for a second predetermined period of time different from the first period of time of a so as to form another pattern in the second surface with a pattern height different from a pattern height of the pattern in the first surface.

A patterned ECM material construct, which can be used, for example, as a biocompatible construct, can be formed by contacting a pattern transfer surface having a degradation agent thereon with a surface of an ECM material. At least a portion of the pattern transfer surface can be coated with a degradation agent. The degradation agent may be an agent that digests and/or degrades the material of the ECM material. For example, the degradation agent may be a protease or an ionic chelator. The degradation agent may be covalently attached to the pattern transfer surface. The pattern transfer surface can include an etch stop region. The etch stop region may be coated with an adhesion inhibiting agent, for example, BSA. The pattern transfer surface may have feature sizes, for example, less than 15-μm. The pattern transfer surface may cover, for example, an area greater than one square centimeter. The pattern transfer surface may be formed on a pattern transfer device made from a polymer material, for example, PDMS, or from a hydrogel, for example, agarose. The pattern transfer surface may be formed on a stamp, roller, block, tile, embossing device, imprinting device, or other pattern transfer device. The ECM material may be a hydrogel, for example, collagen or alginate. The ECM material may be seeded with cells. The ECM material may be seeded with cells prior to or after the contacting. The method may include culturing the cells prior to or after the contacting.

A different pattern transfer surface having a degradation agent can be contacted with the surface of the ECM material. Yet another or the same pattern transfer surface having a degradation agent thereon can be contacted with a second surface of the ECM material different from the surface. The contacting the pattern transfer surface with the surface of the ECM material and the contacting the different pattern transfer surface with the second surface of the ECM material may occur simultaneously or sequentially. A pattern transfer surface can be contacted with the surface of the ECM material for a first predetermined time after which the contacting can be repeated on the same or a different surface for a second predetermined time different than the first predetermined time, whereby features with different pattern heights can be formed in the ECM material.

Figure 7:
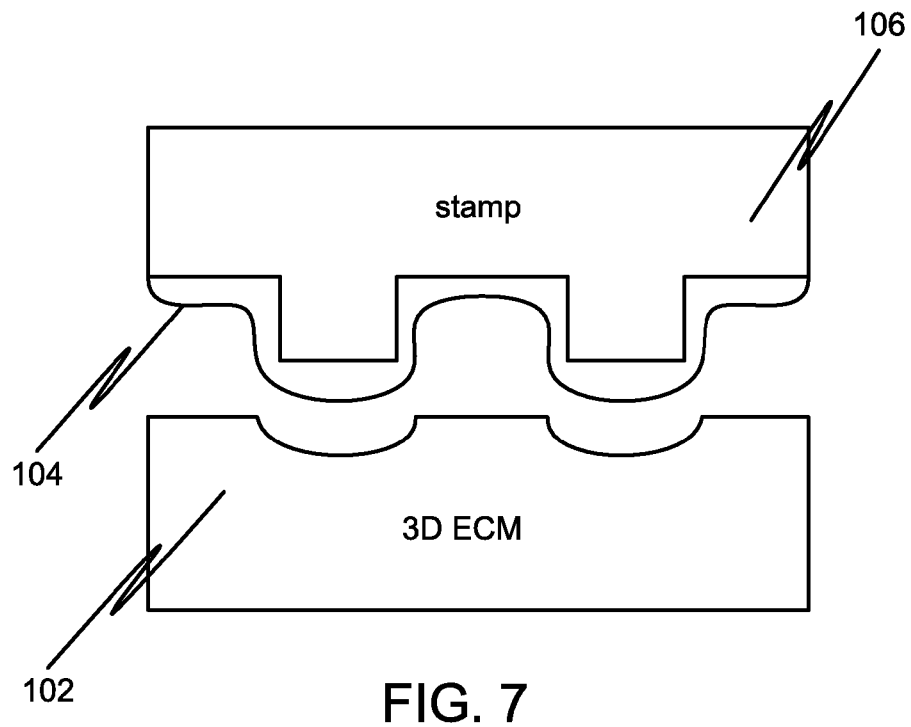
FIG. 7 is a schematic diagram showing a part of a process of patterning a preformed ECM material.

The contact degradation technique offers a simple and robust way to define microstructures in naturally-derived ECM materials, whose cross-links can often be reversed. For example, with reference to FIG. 7A, a pattern transfer device 106, for example, a stamp, with a digestive agent 104 can be placed into contact with a pre-formed 3D ECM material 102. The digestive agents cause localized etching in the 3D ECM material in the form of the pattern, which can have microscale or smaller features, thereby transferring the pattern to the surface of the ECM material in a controlled fashion. The digestive agents may include, for example, proteases (which may be pre-activated with calcium ions) and/or ionic chelators, according to the ECM material of interest. Other digestive agents may also be employed in the disclosed method, depending on the ECM material of interest.

Figure 8:
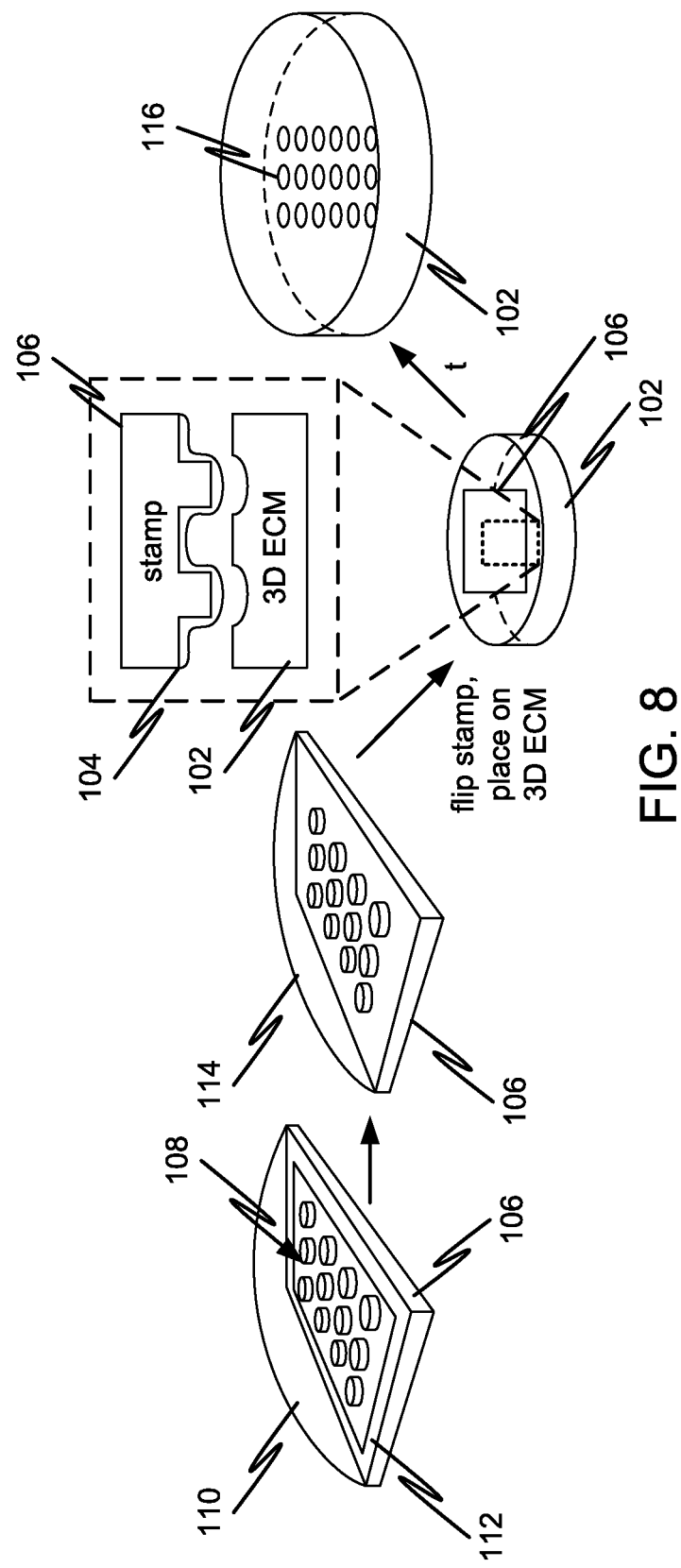
FIG. 8 is a schematic diagram showing a process for patterning a preformed ECM material.

FIG. 8 shows a schematic diagram depicting a method according to one or more disclosed embodiments. A pattern transfer device 106, for example, a stamp, has a pattern 108 on a surface thereof which may be treated with a degradation agent 110, for example, a solution of digestive enzymes and/or ionic chelators. The stamp may be formed, for example, using micro- or nano-fabrication molding techniques on PDMS, other polymer materials, or an ECM material. For example, a transparency mask containing a design with micron-scale feature sizes can be prepared. Using traditional photolithography, a master mold, for example, a silicon mold, with microstructure protrusions can be fabricated. A PDMS base and curing agent can be mixed (e.g., in a 10:1 ratio), degassed, and cured on the master mold (e.g., at 60° C. for 2 hours). The cured PDMS mold can then be prepared and used as a pattern transfer device 106 in the contact degradation process.

Portions of the pattern transfer device outside of a defined pattern transfer region may be masked during treatment with digestive agents so that only the pattern transfer region of the pattern transfer device can be coated with the digestive agents. For example, tape 112 can be placed around the defined pattern transfer region to serve as an "etch stop" to mask transfer and absorption of the digestive agents 110 to the covered regions. After treatment with the digestive agents 110, the masking tape 112 around the pattern transfer region 108 can be removed. The remainder of the pattern transfer device 106 (i.e., outside the pattern transfer area 108) can be treated, for example, with BSA, prior to imprinting the pattern transfer device 106 on the surface of a preformed ECM material 102.

Degradation of the ECM material 102 takes place at the regions of contact, in the shape and size of the pattern features. However, regions that are treated only with BSA serve as an etch stop, such that degradation of the ECM material 102 occurs no more than the full depth of pattern features. The etch stop regions can also prevent adhesion between the pattern transfer device 106 and the ECM material 102 during removal of the pattern transfer device by, for example, mitigating absorption of the ECM material 102 to the pattern transfer device 106.

The pattern transfer device 106 can be transferred onto the surface of a preformed 3D ECM material 102 for a controlled period of time to achieve the desired thickness of the pattern features. To optimize pattern transfer from the pattern transfer device to the ECM material, a flat surface should be maintained in the ECM material and any excessive liquid from the surface should be removed. Furthermore, pattern transfer fidelity may be improved by avoiding air bubbles between the pattern transfer device and the ECM material surface in order to achieve good contact. The pattern transfer device may be brought into contact with the ECM material using manual or automated means. For example, the pattern transfer device could be placed into contact with the ECM material by hand. Alternatively, a manual actuator, a computer or processor controlled actuator, a machine, or a manufacturing tool may be used to contact the pattern transfer device with the ECM material.

Figure 9:
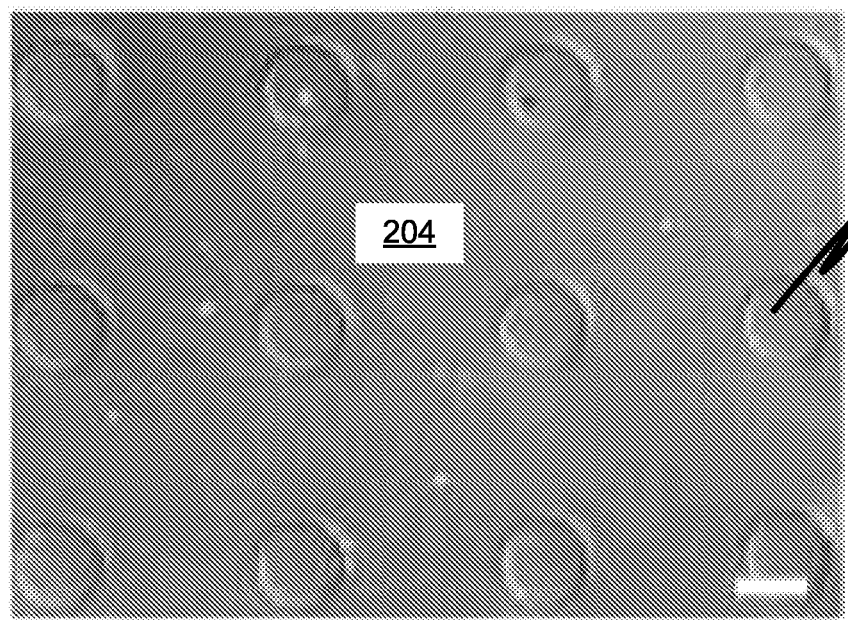
FIG. 9 shows an image of pattern of circular posts patterned into a preformed ECM material.
Figure 10:
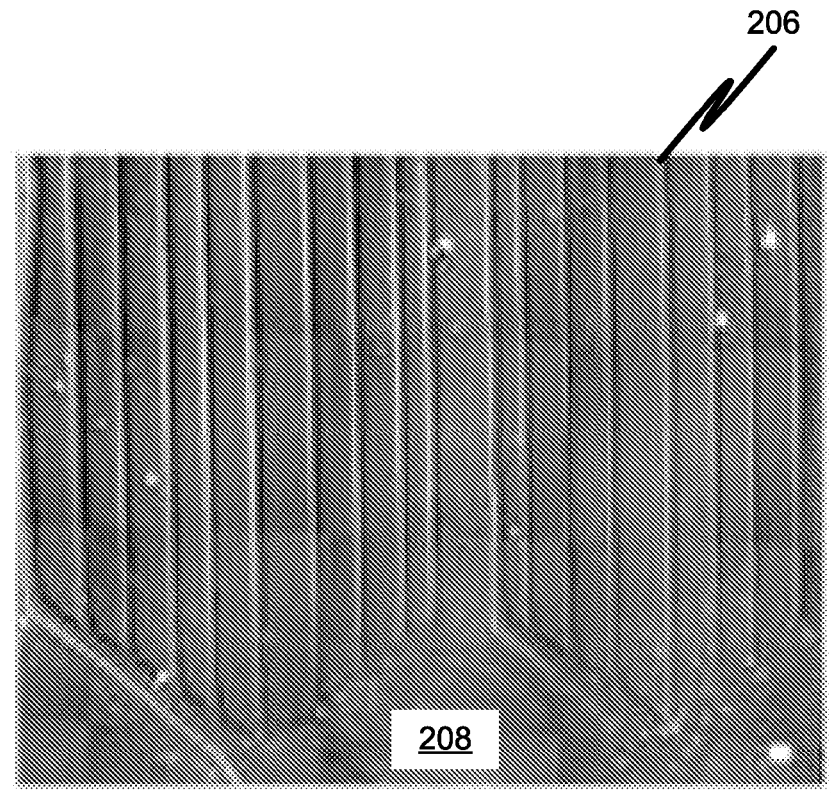
FIG. 10 shows an image of a large scale channel pattern patterned into a preformed ECM material.
Figure 11:
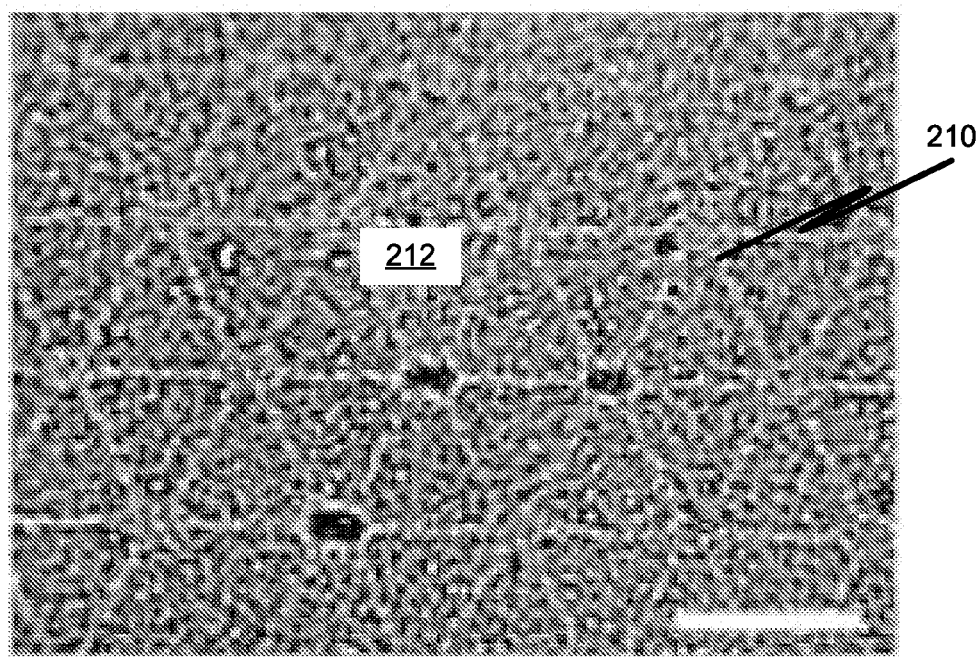
FIG. 11 shows an image of a triangular array pattern patterned into a preformed ECM material.

With reference to FIGS. 9-12, the patterning of type I collagen (for example, 2 mg/ml), the most prevalent structural ECM component in soft tissues, is shown. For degradation of the collagen I ECM shown in FIGS. 9-12, a hydrophobic PDMS stamp was coated by passive adsorption with collagenase, which efficiently degrades collagen I. Three different patterns covering different size scales were used. As shown in FIG. 9, a pattern design of circular posts 202 was microetched into a collagen I ECM 204 using contact degradation. The pattern transfer device had an array of circular pins with a diameter of 120-μm, a height of 120-μm, and a spacing of 220-μm. As shown in FIG. 10, a large centimeter-sized pattern of interconnected microchannels 206 was formed on the surface of a collagen I ECM 208 using contact degradation. As shown in FIG. 11, a high-resolution pattern of interconnected triangles 210 was produced in a collagen I ECM 212 using contact degradation. The three different pattern features (covering three different size scales) illustrate the reliable patterning over large areas (e.g., cm$^2$) with an ability to produce feature sizes less than 15-μm attainable with a contact degradation technique. The feature sizes disclosed herein are only exemplary in nature, and different feature sizes are also attainable using the disclosed techniques with appropriate modification of the pattern features.

Figure 12:
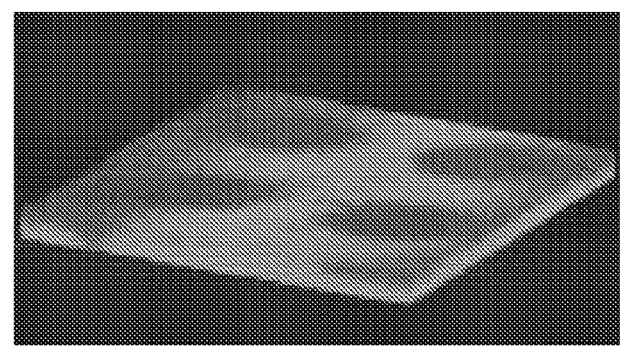
FIG. 12 shows a 3D reconstructed image using confocal laser scanning microscopy of the top of a preformed ECM material after etching with a pattern of circular posts.

FIG. 12 shows a 3D reconstructed image using confocal laser scanning microscopy of the top of a type I collagen gel after etching with a pattern of circular posts. Collagen fibers were imaged using an excitation wavelength at 488-nm and emission filter greater than 500-nm. As shown in FIG. 12, expected geometries with straight sidewall profiles are observed in the etched areas.

Figure 13:
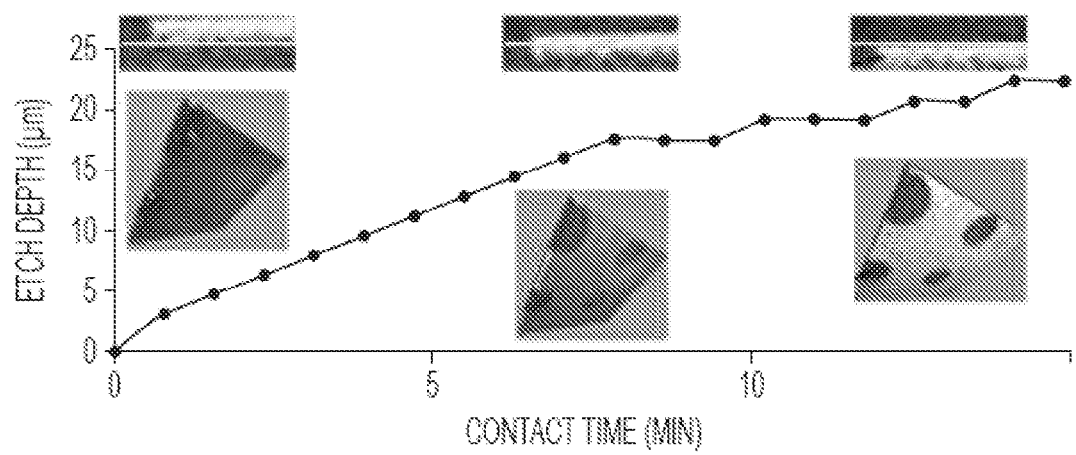
FIG. 13 is an annotated graph illustrating the depth of etching in an ECM material as a function of the duration of contact between a pattern transfer device and the ECM material.

Enzymatic etching can be visualized in real time using confocal laser scanning time-lapse microscopy. Cross-sections of the 3D reconstructed images were used to measure the etching depth at different time points, as shown in FIG. 13. The depth of etching in the ECM material was plotted as a function of the duration of contact between the pattern transfer device and the 3D ECM material. Time-lapse images of the contact degradation process can also be captured via confocal laser scanning microscopy. In FIG. 13, the top inset shows cross-sections of the etching through the ECM material underneath while the bottom inset shows 3D reconstructed images of the ECM material viewed from beneath the pattern transfer device at different time points.

As FIG. 13 illustrates, etch depth linearly increases with contact time until the "etch stop" region contacts the ECM material. This initial linear rate of degradation of the ECM material is consistent with Michaelis-Menten enzyme kinetics. As a fabrication tool, this result also highlights that a single pattern transfer device can be used to produce 3D ECM material features of different heights in a controllable fashion. Thus, by controlling contact time, different feature heights (i.e., etch depths) can be formed in a single 3D ECM material. Other options may also be employed for controlling feature heights in the patterned 3D ECM material, such as using a single pattern transfer device with different feature heights in the pattern.

Figure 14:
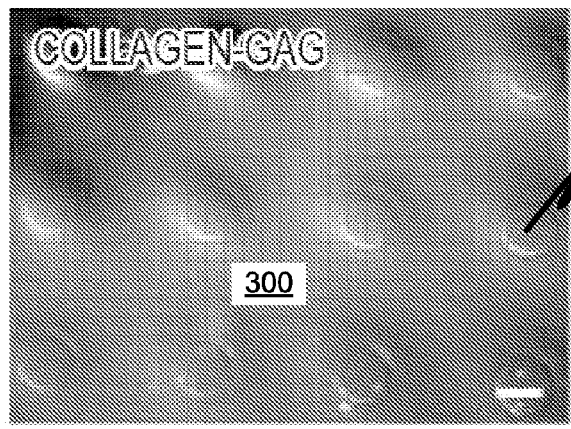
FIG. 14 is an image of a pattern etched into an ECM material of collagen-GAG.

The contact degradation method can also be applied to different types of naturally derived ECM materials, such as, but not limited to, collagen-GAG, Matrigel™, and alginate, by adapting the technique for different mechanisms of degradation A collagen-GAG ECM material can have, for example, 2 mg/mL collagen and 20% GAG. For this ECM material, a PDMS pattern transfer device can be coated with type XI collagenase. As shown in FIG. 14, this pattern transfer device produces patterns 302 in the collagen-GAG 306 with high spatial fidelity.

Figure 15:
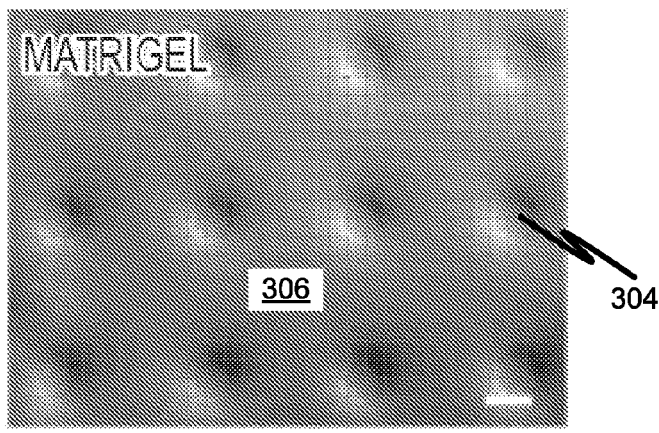
FIG. 15 is an image of a pattern etched into an ECM material of Matrigel™.
Figure 16:
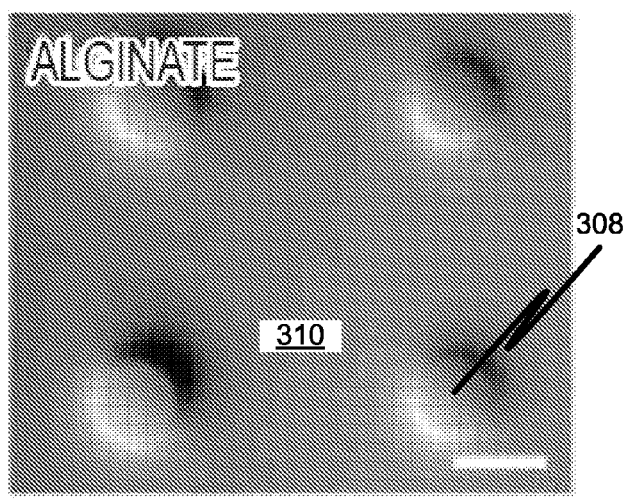
FIG. 16 is an image of a pattern etched into an ECM material of alginate.

For a Matrigel™ ECM material (for example, 8 mg/mL), a PDMS pattern transfer device can be coated with dispase. Dispase hydrolyzes collagen IV, which is a major component of Matrigel™. As shown in FIG. 15, such a pattern transfer device also produces microstructures 304 in the Matrigel™ 306 of high spatial fidelity.

Alginate, a proteoglyan used often for delivery of drugs and growth factors, can also be patterned using a contact degradation technique. Alginate gel (for example, having a concentration of 30 mg/mL) can be made using MVM alginate and 10×PBS. MVM alginate can be allowed to fully dissolve, for example, in 10×PBS for 24 hours. To give the alginate gel its rectangular shape, the dissolved alginate may be poured into a rectangular PDMS gasket placed on top of a glass surface. A dialysis membrane may be immersed, for example, in 10×PBS for 5 minutes, and then laid over the alginate so that the edges of the membrane lay flat on the rectangular gasket. A solution of calcium chloride (for example, 40 mM in 10×PBS) may be poured over the membrane as a cross-linking agent, allowing surface adhesion between the solution and the membrane to hold the solution entirely on the surface of the membrane. The alginate ECM material may be cross-linked with calcium ions, for example, for 1 hour, until it has sufficiently gelled.

For the alginate ECM material (for example, 30 mg/mL), a pattern may be coated with sodium citrate, which degrades the alginate ECM material by sequestering calcium ions and thus breaking down the alginate crosslinks As sodium citrate is a small molecule chelator instead of an enzyme, a pattern transfer device made of another ECM material can be used instead of PDMS. For example, agarose may be used as the material for the pattern transfer device to allow for diffusion of the sodium citrate into the pattern transfer device. The etching time for an alginate ECM material using the agarose pattern transfer device may be, for example, approximately 10 seconds.

Agarose pattern transfer devices can be constructed on silicon masters featuring 'large' circular pins (for example, pin size: 120 μm in diameter, 120 μm in height; pins are 220 μm apart). A mixture of pure agarose (for example, 40 mg/mL) and sodium citrate (for example, 40 mM) in distilled water can be boiled, after which the boiled agarose mixture can be immediately poured onto a silicon master mold. The mixture can be allowed to gel as it cooled to room temperature. The cooled agarose gel from the silicon master mold can be used as a pattern transfer device. Using a contact degradation technique with the agarose pattern transfer device and the sodium citrate as the degradation agent, micropatterned 3D alginate microstructures 308 can be formed in the alginate ECM, as shown in FIG. 3C.

An application of the techniques disclosed herein can include fabricating microscale and/or nanoscale features within pre-existing 3D cell-seeded ECM material constructs. Additive methods for fabricating 3D constructs involve mixing cells with a natural or synthetic ECM material precursors and gelling the mixture through heat, light, addition of ions, or change in pH into desired 3D ECM material shapes. However, such additive techniques may inhibit the study of the effects of geometrical constraints on latter stages of 3D tissue culture, cell migration, and tissue morphogenesis.

The contact degradation technique disclosed herein can be used to introduce structural changes into cellular constructs after cell spreading, migration, and remodeling of the ECM materials have taken place, i.e., at advanced stages of biological processes. For example, 3T3 fibroblasts can be encapsulated within an ECM material, such as type I collagen gel. 3T3 fibroblasts may be passed under 5% CO2 at 37° C. in Dulbecco's modified essential medium (DMEM) adjusted to 4 mM L-glutamine, 1.5 g L-1 sodium bicarbonate, 4.5 g L-1 glucose, supplemented with 10% bovine calf serum and 1% penicillin/streptomycin, and used at 80% confluence. A suspension of fibroblasts and type I collagen can be mixed (for example, in a ratio of 1:1) to make an ECM material with a final collagen concentration of, for example, 2 mg/mL and cell density of, for example, $1\times10^5$ cells/ml. After the fibroblasts-embedded collagen is completely gelled (for example, at 37° C. for 1.5 hours), cell media can be added on top of the gel.

Figure 17:
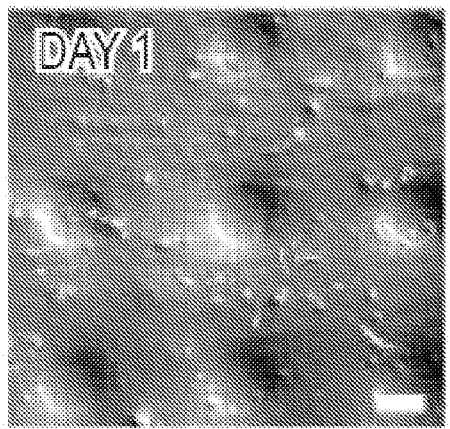
FIG. 17 is an image of a pattern etched into a cell-embedded ECM material after culturing for 1 day.
Figure 18:
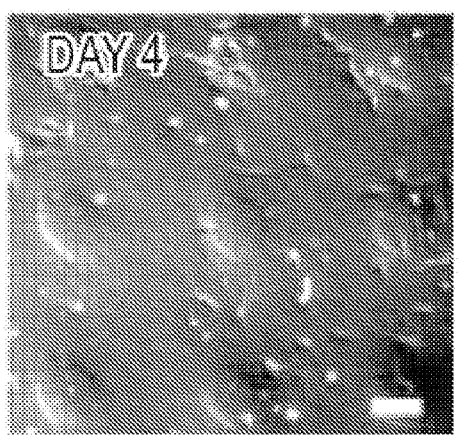
FIG. 18 is an image of a pattern etched into a cell-embedded ECM material after culturing for 4 days.
Figure 19:
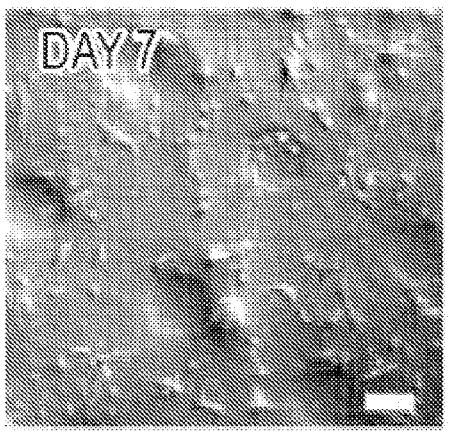
FIG. 19 is an image of a pattern etched into a cell-embedded ECM material after culturing for 7 days.

The cell-seeded collagen gel can then be stamped with collagenase-treated pattern transfer device at multiple time points. As shown in FIGS. 17-19, sharply defined features can be formed using the disclosed contact degradation technique within cell-encapsulated collagen gels that had been cultured for numerous days. Constructs of type I collagen embedded with 3T3 fibroblasts were microetched through contact degradation after culturing for 1 day (2 hours etching) (FIG. 17), 4 days (2 hours etching) (FIG. 18), and 7 days (3 hours etching) (FIG. 19). Etching can be performed at 37° C. for 2 hours on days 1 and 4 of the cell culture, and 3 hours on day 7 of the cell culture. The rate of etching for a given stamp contact time can be reduced significantly as the duration of the culture increases, potentially due to the increased collagen content and increased amount of crosslinks between collagen fibers and collagen synthesized by fibroblasts.

Moreover, to assess the effect of enzymatic etching of the ECM material on the encapsulated mammalian cells, cell viability of the fibroblasts was examined after enzymatic etching. A cell-embedded ECM material with 2 mg/mL of type I collagen and cell density of 1×10$^5$ cells/mL was prepared. After 24 hours of culture, the cell-embedded collagen was etched for 3 hours at 37° C. Both unetched (control) and etched (experimental) ECM materials were stained with LIVE/DEAD Viability/Cytotoxicity Kit for 30 minutes at room temperature. Fluorescent images were taken across the surface of the gel and the total number of viable (dark grey) and dead (white) cells were counted.

Figure 20:
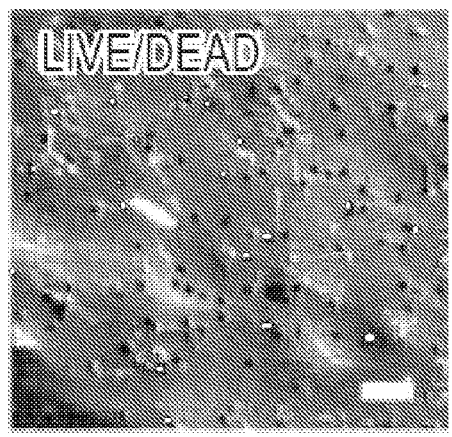
FIG. 20 is an image showing cell viability using a LIVE/DEAD stain in an etched cell-embedded ECM material after culturing for 1 day.

An image of cell-embedded ECM materials (at Day 1 culture) after 3 hours of etching illustrating cell viability after contact degradation is shown in FIG. 20. As shown, there is essentially no effect on viability of the cells in the micro-etched ECM material. Approximately 88% of the cells in the regions that were contacted with collagenase were alive, compared with approximately 89% in other regions. This ability to input structural alterations into a 3D culture system at advanced stages without adversely affecting cell viability can lead to new insights into the role of geometric constraints in microenvironment on cellular migration and tissue morphogenesis.

The disclosed contact degradation technique may also be applied to the formation of composite 3D ECM materials and complex composite structures, which may be relevant for tissue and/or organ engineering. For example, in one method a composite ECM material may be formed by forming a first ECM material and contacting a surface of the first ECM material with a pattern transfer surface coated with a degradation agent so as to form a pattern in the first ECM material surface. A second ECM material can be formed in the pattern in the first ECM material surface. A pattern transfer surface coated with a degradation agent can be contacted with a surface of the second ECM material so as to form a pattern in the second ECM material surface. The first and second ECM materials can be formed adjacent to each other or the second ECM material can be formed in at least recessed portions of the first ECM material pattern. The first and second ECM materials can be of the same or different types. The first and second ECM materials can be hydrogels. The first and/or second ECM materials can be seeded with cells. The first and/or second ECM materials seeded with cells can be incubated. The contacting of the surface of the at least one of the first and second ECM materials seeded with cells with a pattern transfer surface coated with a degradation agent can be repeated so as to form a pattern therein, before or after the incubating.

A third ECM material can be formed in at least a recessed portion in at least one of the patterns in the first and second ECM material surfaces or to cover at least a portion of at least one of the first and second ECM material surfaces. At least one of the first, second, and third ECM materials can be a different type. At least one of the first, second, and third ECM materials may be seeded with cells. Cells in at least one of the first, second, and third ECM materials may be different than cells in at least another of the first, second, and third ECM materials. As above, the at least one of the first, second, and third ECM materials seeded with cells can be incubated. Before or after the incubating, the contacting of the surface of the at least one of the first, second, and third ECM materials seeded with cells with a pattern transfer surface coated with a degradation agent can be repeated so as to form a pattern therein. This method may be repeated (i.e., forming and the degradation contacting multiple times) to form a composite ECM construct with multiple patterned gel components.

A composite ECM material can also be formed by providing a first ECM material with a pattern on a surface thereof and forming in at least the first ECM material surface pattern a second ECM material. The first ECM material surface pattern can include a microfluidic channel network. A pattern can be etched into a surface of the second ECM material by contacting with a pattern transfer device. The pattern transfer device can have a patterned surface coated with a component that degrades or digests the second ECM material. The pattern transfer device can be a stamp, roller, block, tile, embossing device, or imprinting device. A third ECM material can be formed in at least the second ECM material surface pattern. At least one of the first, second, and third ECM materials can be seeded with cells and incubated. Before or after the incubating, a pattern can be etched into a surface of the at least one of the first, second, and third ECM materials seeded with cells by contacting with a pattern transfer device.

An ECM construct, which may serve as an engineered tissue construct, can include a main ECM component with a first pattern and at least one minor ECM material formed in at least a portion of the first pattern. More than one minor ECM material may be formed in the first pattern. At least one of the minor ECM materials may be different from another of the minor ECM materials. The first pattern in the main ECM material may be a microfluidic channel network. The at least one minor ECM material may be formed in the microfluidic channel network. The degrading surface may etch a pattern into a surface of at least one of the main and the minor ECM materials.

Figure 21:
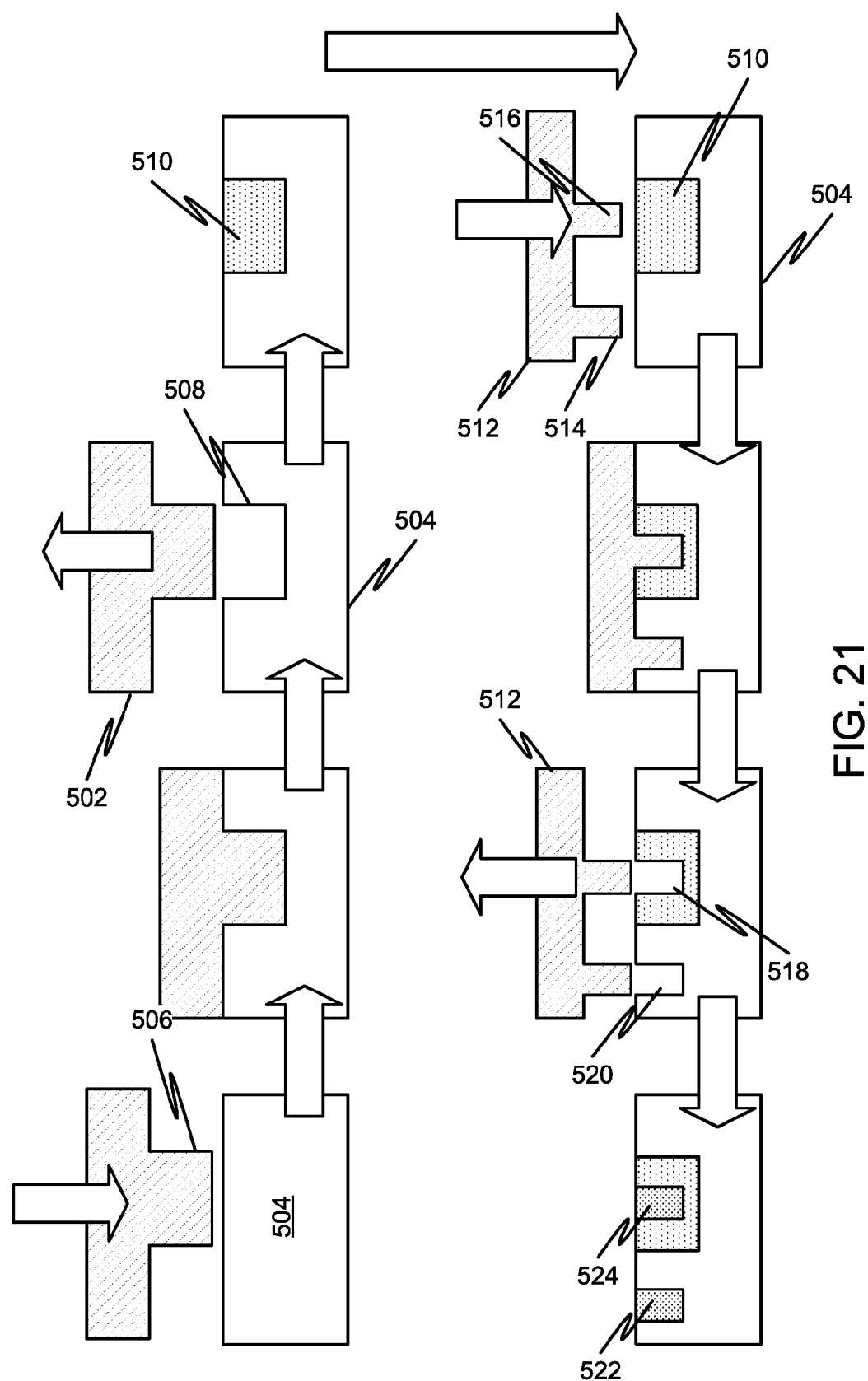
FIG. 21 is a schematic diagram showing a process flow for creating a composite ECM material using a contact degradation technique.

With reference to FIG. 21, a first ECM material 504 may be formed with a pattern 508 on a surface thereof. The pattern 508 can be formed by contacting a pattern transfer device 502 with a pattern 506 and a degradation coating (not shown) with the ECM material 504. It is noted that the first ECM material may also be provided with the pattern 508 already formed therein by a technique other than the disclosed contact degradation technique. For example, the first ECM material may be gelled on a mold such that the pattern is created on a surface thereof during the gelling process. Additionally or alternatively, the first ECM material may be formed in a microfabricated bioreactor 1000, as described above with regard to FIG. 1B.

A second ECM material 510 can be formed in the recessed portions of the pattern 508 formed in the first ECM material 504. For example, the pattern in the first ECM material can take the form of a microfluidic channel network. The second ECM material precursors can be flowed through the network and gelled in situ to create the second ECM material in the pattern 508. In another example, the pattern in the first ECM material may take the form of isolated regions on the surface of the first ECM material. In this example, the second ECM material may be formed in the pattern by, for example, applying gel precursors to the surface of the first ECM material, removing excess precursors from the surface of the first ECM material, and gelling the precursors within the pattern.

The patterning and formation processes can be repeated any number of times with various ECM materials. For example, a second pattern transfer device 512 with a patterned region 516 and a degradation coating (not shown) can be brought into contact with the ECM material 510 to effect the formation of a pattern 518. The pattern transfer device 512 can also be used to simultaneously introduce an additional pattern 520 into the first ECM material 504. For example, stamp 512 can include a patterned region 514. When the stamp 512 is aligned with the ECM materials, patterned region 516 contacts the second ECM material 510 while patterned region 514 contacts the first ECM material 504. Thus, patterns 518 and 520 may be simultaneously produced in the respective ECM materials.

Figure 22:
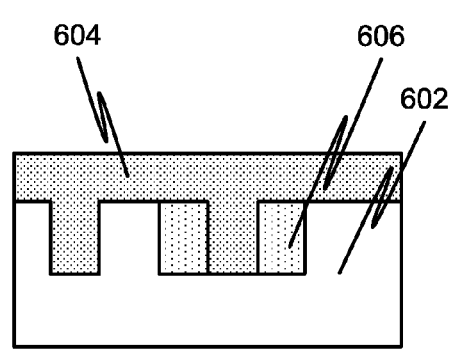
FIG. 22 is an example of structure for a composite ECM material formed using a contact degradation technique.

Within the second ECM material pattern 518, a third ECM material 524 may be formed, similar to the process discussed above with regard to the second ECM material. An ECM material 522 may also be introduced into the newly formed pattern 520 in the first ECM material 504. ECM materials 522 and 524 may be the same or different types of ECM materials. The configuration of the structures attainable with the present technique is not limited to the nested structures shown in FIG. 21. For example, the third ECM material may be deposited to extend across the entire surface of the first ECM material in addition to filling the patterns 518 and 520. Such a structure is shown in FIG. 22, in which a third ECM material 604 covers and extends into both the patterns in the first ECM material 602 and the second ECM material 606.

Figure 23:
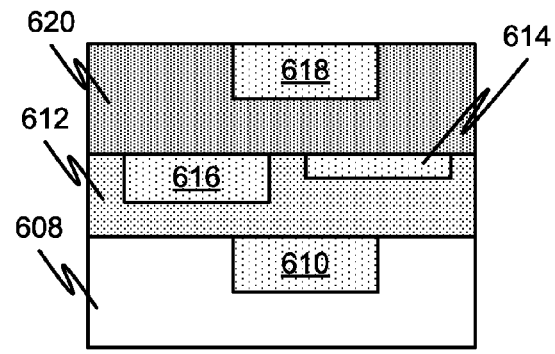
FIG. 23 is another example of structure for a composite ECM material formed using a contact degradation technique.

The technique of FIG. 21 can be repeated numerous times to build up a composite structure of individual ECM materials. For example, such a composite ECM material structure is shown in FIG. 23. A first ECM material 608 can be formed with a second ECM material 610 in a pattern in the first ECM material 608, similar to the process illustrated in FIG. 21. A third ECM material 612 may be formed on a surface of the first ECM material 608, similar to the arrangement of FIG. 22. This third ECM material 612 may itself be patterned using the disclosed contact degradation technique. A fourth ECM material 614 may be formed in the pattern in the third ECM material 612.

As previously discussed, since the time of contact between the pattern transfer device and the ECM material determines the etch depth (and thus the depth of the pattern), patterns of different depths may be formed in the same ECM material by using different contact times. Thus, a second pattern may be formed in the third ECM material which has a different depth from the other formed pattern. A fifth ECM material 616 may be formed in the second pattern in the third ECM material 612. A sixth ECM material 620 may be formed on a surface of the third ECM material 612, similar to the arrangement of FIG. 22. The sixth ECM material 620 may itself be patterned using the disclosed contact degradation technique. A seventh ECM material 618 may then be formed in the pattern in the sixth ECM material 620. This process can be repeated indefinitely to form a multilayer composite ECM material structure.

The ECM materials in the composite ECM material structure may be different or the same type. One or more of the ECM materials in the composite ECM material structure may be seeded with cells. Individual ECM materials in the composite structure may be seeded with the same or different types of cells. If seeded with cells, the patterning using the contact degradation method can be employed before or after incubation. For example, the cells in one (or more) of the ECM materials of the composite ECM material structure can be incubated for a predetermined period of time, after which the cell-seeded ECM material (and/or other ECM materials of the structure) is patterned using the disclosed contact degradation technique. As previously discussed, such a setup can be used to study the impact of ECM material structural changes on developing cells.

The contact degradation technique disclosed herein can be achieved by providing enzymes on a pattern transfer device by passive adsorption, as discussed above. However, other methods for providing the pattern transfer device with a degradation/digestive agent can also be employed. For example, the enzyme can be covalently bonded or attached to the pattern transfer device. Furthermore, while disclosed examples for fabrication of the pattern transfer device include micromolding of PDMS and agarose, other fabrication techniques can also be applied to other materials to form the pattern transfer device. For example, micromachined polymers, semiconductors, or devices may be formed by microprinting, hot embossing, laser machining, focused ion beam etching, photolithographic wet etching, photolithographic dry etching, or other methods known in the applicable arts can be used to form the pattern transfer device.

Although particular concentrations and compositions have been discussed herein, one of ordinary skill in the applicable arts will appreciate that other concentrations and compositions can also be employed. Furthermore, the foregoing descriptions apply, in some cases, to examples generated in a laboratory, but these examples can be extended to production techniques. For example, where quantities and techniques apply to the laboratory examples, they should not be understood as limiting.

It is, thus, apparent that there is provided, in accordance with the present disclosure systems, methods and devices for forming patterned ECM materials. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

The invention claimed is:

1. A biocompatible skin substitute, comprising:
a gel first layer having a top surface and a bottom surface, a thickness of the gel first layer being from the top surface to the bottom surface, a length of the gel first layer being in a direction perpendicular to said thickness, the thickness being less than said length,
the gel first layer including a plurality of substantially discontinuous cylindrical zones, each zone extending entirely through the thickness of the gel first layer from the top surface to the bottom surface;
the zones being substantially regularly spaced and having a mean diameter of between 70 and 120-μm such that the gel first layer has a void fraction between 20% and 60%;
an average density of fibers in each zone being lower than an average density of fibers in the gel first layer between the zones;
an average distribution of fibers in the gel first layer being uniform across the thickness of the gel first layer; and
the fibers including collagen and a glycosaminoglycan containing chondroitin-6-sulfate,
wherein the respective densities of the fibers in the zones and between the zones permits freer migration of human epithelial dermal cells into the zones than between the zones.

2. The substitute of claim 1, wherein the average density of fibers in each zone is zero.

3. The substitute of claim 1, wherein the thickness of the gel first layer is less than or equal to 120 μm and the length is at least 1 cm.

4. An engineered tissue structure comprising:
a gel first layer having a top surface and a bottom surface, a thickness of the gel first layer being from the top surface to the bottom surface, a length of the gel first layer being in a direction perpendicular to said thickness, the thickness being less than said length,
the gel first layer including a plurality of substantially discontinuous zones,
wherein an average density of fibers in each zone is lower than an average density of fibers in the gel first layer between the zones, an average distribution of fibers in the gel first layer is uniform along a direction parallel to the thickness of the gel first layer, and each zone extends entirely through the thickness of the gel first layer from the top surface to the bottom surface.

5. The engineered tissue structure according to claim 4, wherein the zones are substantially regularly spaced.

6. The engineered tissue structure according to claim 4, wherein the fibers include a protein and a glycosaminoglycan.

7. The engineered tissue structure according to claim 6, wherein the protein includes collagen.

8. The engineered tissue structure according to claim 6, wherein the glycosaminoglycan includes chondroitin-6-sulfate.

9. The engineered tissue structure according to claim 4, wherein the respective densities of the fibers in the zones and between the zones permits freer migration of human epithelial dermal cells into the zones than between the zones.

10. The engineered tissue structure according to claim 4, further comprising a gel second layer adjacent to the gel first layer at a first side thereof, wherein each zone extends entirely through the thickness of the gel first layer so as to connect, through each zone, the second layer with a second side opposite said first side.

11. The engineered tissue structure according to claim 10, wherein an average density of fibers in the gel second layer is lower than an average density of fibers in the gel first layer between the zones.

12. The engineered tissue structure according to claim 4, wherein the average density of fibers in each zone is zero.

13. The engineered tissue structure according to claim 4, further comprising a backing layer with a respective average density of fibers that is lower than the average density of fibers between the zones.

14. The engineered tissue structure according to claim 4, further comprising:

a backing supporting the gel first layer thereon, wherein the gel first layer includes a first extracellular matrix with said fibers therein, the plurality of discontinuous zones form a pattern in the first extracellular matrix extending through the thickness of the gel first layer.

15. The engineered tissue structure according to claim 14, wherein the pattern comprises pores.

16. The engineered tissue structure according to claim 15, wherein the gel first layer has a mean pore size from 20 μm to 125 μm and a void fraction from 20% to 60%.

17. The engineered tissue structure according to claim 14, wherein the first extracellular matrix includes collagen.

18. The engineered tissue structure according to claim 14, wherein the first extracellular matrix includes collagen and glycosaminoglycan.

19. The engineered tissue structure according to claim 14, further comprising a gel second layer of second extracellular matrix different from the first extracellular matrix supported on a side of the gel first layer.

20. The engineered tissue structure according to claim 19, wherein the first extracellular matrix includes collagen.

21. The engineered tissue structure according to claim 20, wherein the second extracellular matrix includes a hydrogel.

22. The engineered tissue structure according to claim 4, wherein the plurality of substantially discontinuous zones are cylindrical and extend entirely through the thickness of the gel first layer, the zones are substantially regularly spaced such that the gel first layer has a void fraction of approximately 20% to 60%, each zone has an average diameter of between 70 μm and 120 μm, the fibers include collagen and a glycosaminoglycan containing chondroitin-6-sulfate, and the respective densities of the fibers in the zones and between the zones permits freer migration of human epithelial dermal cells into the zones than between the zones.

* * * * *